US 10,781,214 B2

(12) United States Patent
Liu et al.

(10) Patent No.: US 10,781,214 B2
(45) Date of Patent: Sep. 22, 2020

(54) KINASE INHIBITOR AGAINST WILD-TYPE AND MUTANT EGFR

(71) Applicant: PRECEDO PHARMACEUTICALS CO., LTD, Hefei, Anhui (CN)

(72) Inventors: Qingsong Liu, Anhui (CN); Jing Liu, Anhui (CN); Xixiang Li, Anhui (CN); Aoli Wang, Anhui (CN); Hong Wu, Anhui (CN); Kailin Yu, Anhui (CN); Chen Hu, Anhui (CN); Wenchao Wang, Anhui (CN); Cheng Chen, Anhui (CN); Fengming Zou, Anhui (CN); Ziping Qi, Anhui (CN); Li Wang, Anhui (CN); Beilei Wang, Anhui (CN)

(73) Assignee: PRECEDO PHARMACEUTICALS CO., LTD., Hefei, Anhui (CN)

( * ) Notice: Subject to any disclaimer, the term of this patent is extended or adjusted under 35 U.S.C. 154(b) by 0 days.

(21) Appl. No.: 16/066,427

(22) PCT Filed: Dec. 27, 2016

(86) PCT No.: PCT/CN2016/112322
§ 371 (c)(1),
(2) Date: Jun. 27, 2018

(87) PCT Pub. No.: WO2017/114383
PCT Pub. Date: Jun. 7, 2017

(65) Prior Publication Data
US 2019/0010159 A1   Jan. 10, 2019

(30) Foreign Application Priority Data

Dec. 31, 2015   (CN) ........................... 2015 1 1030721

(51) Int. Cl.
*C07D 487/04* (2006.01)
*A61K 31/519* (2006.01)
*A61P 35/00* (2006.01)
(52) U.S. Cl.
CPC .......... *C07D 487/04* (2013.01); *A61K 31/519* (2013.01); *A61P 35/00* (2018.01)
(58) Field of Classification Search
CPC ............................. C07D 487/04; A61K 31/519
See application file for complete search history.

(56) References Cited

U.S. PATENT DOCUMENTS 8,377,946 B1    2/2013  Chen et al.
2010/0144705 A1  6/2010  Miller

FOREIGN PATENT DOCUMENTS

WO    2014/188173 A1    11/2014
WO    WO-2014187319 A1 * 11/2014 ........... A61K 31/519

OTHER PUBLICATIONS

Wheeler, Deric. Nat. Rev. Clin. Oncol. 7, 493-507 (2010).*
MedicineNet.com (2004) Web: http://www.medterms.com.*
Banker. Gilbert. Modern Pharmaceutics 3rd ed. Marcel Dekker, Inc. New York, 1996.*
International Search Report dated Mar. 27, 2017 issued in PCT/CN2016/112322.
Schiller, Joan H. et al., "Comparison of Four Chemotherapy Regimens for Advanced Non-Small-Cell Lung Cancer", The New England Journal of Medicine (Jan. 10, 2002), vol. 346, No. 2, pp. 92-98.
Yun, Cai-Hong et al., "The T790M mutation in EGFR kinase causes drug resistance by increasing the affinity for ATP", PNAS (Feb. 12, 2008), vol. 105, No. 6, pp. 2070-2075.
Zapf C.W. et al., "Covalent Inhibitors of Interleukin-2 Inducible T Cell Kinase (Itk) With Nanomolar Potency in a Whole-Blood Assay", Journal of Medicinal Chemistry 55(22)10047-10063 (Nov. 26, 2012).
Extended Supplementary European Search Report dated Jun. 17, 2019 received in European Application No. 16 88 1172.7.
English-language translation of International Preliminary Report on Patentability dated Jun. 7, 2018 received in International Application No. PCT/CN2016/112322.

* cited by examiner

*Primary Examiner* — Emily A Bernhardt
*Assistant Examiner* — Laura M Daniel
(74) *Attorney, Agent, or Firm* — Scully, Scott, Murphy & Presser, P.C.

(57) ABSTRACT

The present application provides a compound of Formula (I) as an inhibitor against wild-type EGFR and/or mutant EGFR, which may be used for treating human non-small cell lung cancer individually or in combination with other therapeutic agent(s). The compound of Formula (I) of the present application may be used for treating patients of drug-resistant human non-small cell lung cancer harboring wild-type EGFR and/or EGFR T790M mutation and/or EGFR L858R mutation and/or EGFR delE746_A750 mutation.

Formula (I)

11 Claims, 11 Drawing Sheets

KINASE INHIBITOR AGAINST WILD-TYPE AND MUTANT EGFR

TECHNICAL FIELD

The present invention relates to a novel kinase inhibitor against wild-type and mutant EGFR and its use in treating non-small cell lung cancer, especially drug-resistant non-small cell lung cancer with EGFR T790M mutation and/or EGFR L858R mutation and/or EGFR delE746_A750 mutation.

BACKGROUND OF THE INVENTION

Lung cancer is a clinically common malignancy in lung, which is generally divided into two categories: small cell lung cancer (SCLC) and non-small cell lung cancer (NSCLC). The incidence of non-small cell lung cancer in the world has been increasing year by year, which seriously threatens human health. Non-small cell lung cancer is the leading cause of cancer deaths in the United States, Japan, and Western Europe. For patients with advanced cancer, although chemotherapy may improve survival to a certain extent, chemotherapeutic agents may have significant toxicity to humans. Therefore, there is a great need for therapeutic agents that can specifically target key genes involved in tumor growth (Schiller J H et al., *N. Engl. J. Med.,* 346: 92-98, 2002).

The gene mutation of EGFR in NSCLCL mainly occurs in the first four exons of the intracellular TK region (18 to 21). More than 30 mutations in the TK region have been reported so far. The main mutations include: deletion mutation at exon 19, point mutation at codon 719 (GT19X), insertion mutation at exon 20, and exon 221-amino steroid (aminosteroid). Deletion mutation at exon 19 includes deletion of leucine-747 to glutamic acid-749, which is located at the N-terminus of the C-helical region of tyrosine kinase, which accounts for approximately 44%. The mutation at exon 20 accounts for about 5% and G719X accounts for 4%. Point mutation at exon 21 is the most common point mutation in the EGFRTK region, accounting for approximately 41%. Gene mutations in EGFR tyrosine kinase domain were detected in tumor tissue specimens collected from 31 patients with advanced NSCLC. The results showed that a total of 12 instances of gene mutations were detected, wherein 4 were chromosome 19 deletion, of which 3 instances had amino acid changes from E746 to A750 caused by 2235-2249 nucleotide deletion and 1 instance had amino acid change of L747-P753insS (deletion of 747 leucine to 753 phenylalanine with insertion of serine) caused by 2240-2257 nucleotide deletion; 8 cases had missense mutations on chromosome 21, all of which were L858R (T>G) mutations, but no mutations were found on chromosome 18 and 20. Tokumo et al. reported that most of the EGFR mutations in exons 18 to 21 from 120 surgically resected NSCLC samples were found to be exon 19 deletion and point mutation in exon 21 (L858R), which could result in increased activity of EGFR tyrosine kinases while simultaneously activate different signaling pathways. Studies have shown that expression of EGFR is upregulated in 43% to 89% of non-small cell lung cancer (NSCLC), and it plays an important role in formation of tumors and biological behavior of tumor cells medicated by EGFR, and is one of the important targets in treatment of NSCLC. Therefore, studying the specific mechanism of EGFR mutations in the pathogenesis of NSCLC is of crucial importance to the treatment, prognosis and survival time of EGFR-TKI.

Activating EGFR mutations are located in tyrosine kinase domain and can result in constitutive EGFR signaling. EGFR mutation-activated PI3K-AKT and RAS-MEK-ERK signals play a crucial role in the growth, survival and migration of cancer cells. The most common activating mutations are an in-frame deletion of exon 19 and a missense mutation of the 858 codon (resulting in the substitution of leucine by arginine, L858R). Lung cancers with EGFR mutations are highly sensitive to EGFR tyrosine kinase inhibitors (TKIs). Currently, genotypic screening of EGFR mutations is often used to screen patients with stage IV NSCLC for whom the first-line therapy may be EGFR TKIs. Current research focuses on prolonging the duration of the response and finding effective ways to target mechanism of drug resistance that is developed during disease progression. The most common mechanism of drug resistance is EGFR/T790M mutation, which is present in about 50% of drug-resistant tumors. In addition, there have been several other mechanisms such as MET amplification, PIK3CA mutation, and transformation to SCLC.

Currently, medicaments including tyrosine kinase inhibitors (TKIs) targeting EGFR (e.g., Iressa (Gefitinib) and Tarceva (erlotinib)) have achieved great success in clinical treatment of non-small cell lung cancer. However, patients treated with TKI inhibitors are often faced with relapse due to the development of TKI resistance. Second-generation EGFR irreversible inhibitors such as Canertinib, Afatinib, Neratinib, Pelitinib have entered clinical trials, but these molecules have poor selectivity for EGFR mutants, resulting in lower clinically-tolerated doses of the medicines. As a result, these medicines fail to reach an effective concentration in the body under the maximum tolerated dose and are therefore ineffective for most drug-resistant patients.

In addition, studies have shown that in the treatment of EGFR-TKI-sensitive non-small cell lung cancer (NSCLC) with Gefitinib or Erlotinib, patients often develop secondary resistance after 6 to 12 months, wherein about 50% contains T790M mutation encoded by exon 20. Studies have suggested that T790M mutation impedes the binding of EGFR to small EGFR inhibitors (such as Gefitinib and Erlotinib) or increases the affinity of EGFR and ATP, leading to drug resistance (Yun C H et al., *Proc. Natl. Acad. Sci. USA.* 2008 Feb. 12; 105(6):2070-5).

SUMMARY OF THE INVENTION

In one aspect, the present application provides a compound of Formula (I) or its pharmaceutically acceptable salts, solvates, isomers, esters, acids, metabolites or prodrugs:

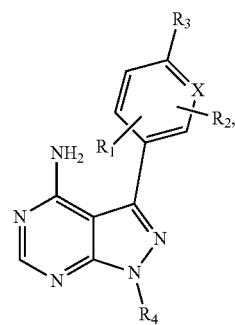

Formula (I)

wherein, X is selected from the group consisting of C and N;
each of $R_1$ and $R_2$ is independently selected from the group consisting of hydrogen, halogen, $C_{1-8}$ alkyl, $C_{1-8}$ haloalkyl, $C_{1-8}$ alkoxy, cyano, and heterocyclylcarbonyl;
$R_3$ is selected from the group consisting of hydrogen, halogen, arylalkoxy, heteroarylalkoxy, heterocyclylalkyl, heterocyclylcarbonyl, or —CO—NH—$(CH_2)_n$-heterocyclyl, wherein n is an integer selected from 0-3, and $R_3$ may be optionally substituted with 1-3 independent $R_6$;
$R_4$ is selected from the group consisting of

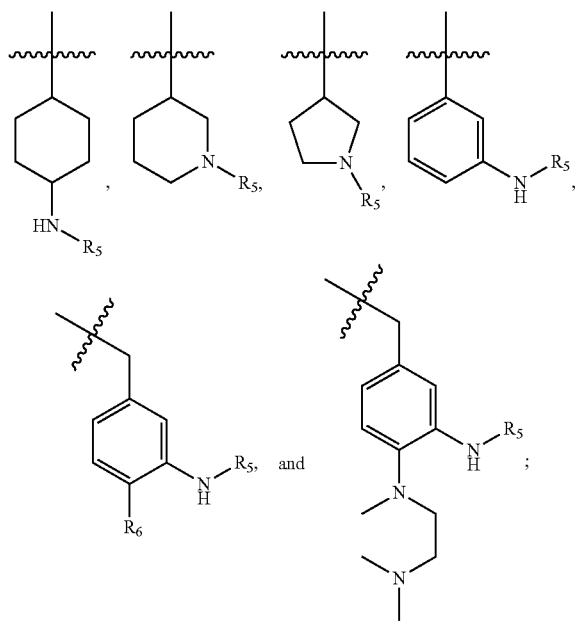

$R_5$ is selected from the group consisting of

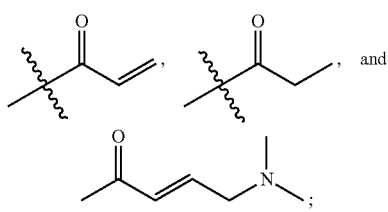

each $R_6$ is independently selected from the group consisting of hydrogen, halogen, $C_{1-8}$ alkyl, $C_{1-8}$ haloalkyl, $C_{1-8}$ alkoxy, cyano, and methanesulfonyl.

The present invention also relates to a pharmaceutical composition comprising the above compound, a method for prevention or treatment of diseases, disorders, or conditions, or autoimmune diseases modulated by or otherwise affected by tyrosine kinase activity or in which tyrosine kinase activity is implicated by using said compound, as well as use of the compound in the above prevention or treatment.

DESCRIPTION OF THE FIGURES

FIG. 2b: H1975 cells; FIG. 2c: H3255 cells; FIG. 2d: HCC827 cells; FIG. 2e: A549 cells);

FIG. 4 illustrates the experimental results obtained by treating mouse tumor models of non-small cell lung cancer cells PC-9 with different concentrations of Compound 1 and the solvent control, wherein

FIG. 5 illustrates the experimental results obtained by treating mouse tumor models of non-small cell lung cancer cells H1975 with different concentrations of Compound 1 and the solvent control, wherein

DETAILED DESCRIPTION OF THE INVENTION

Terminology

Figure 1A:
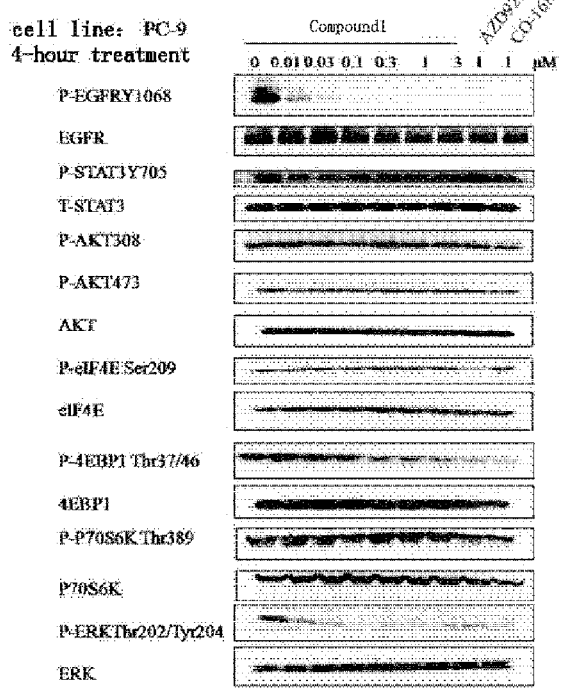
FIG. 1 is a drawing of signaling which illustrates the effects of Compound 1, Compound 29 and Compound 37 on phosphorylation of different signaling-relevant proteins in various cells (FIG. 1a: Compound 1/PC-9 cells.
FIG. 1b: Compound 1/H1975 cells.
FIG. 1c: Compound 1/H3255 cells.
FIG. 1d: Compound 1/HCC827 cells.
FIG. 1e: Compound 1/A549 cells.
FIG. 1f: Compound 29/H1975 cells.
FIG. 1g: Compound 29/PC-9 cells.
FIG. 1h: Compound 29/HCC827 cells.
FIG. 1i: Compound 29/H3255 cells.
FIG. 1j: Compound 37/H3255 cells).
Figure 1B:
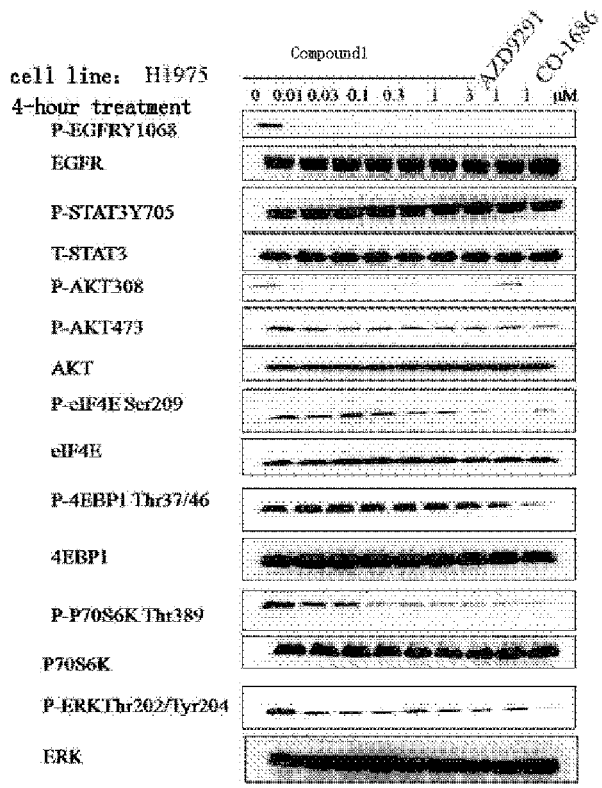
Figure 1C:
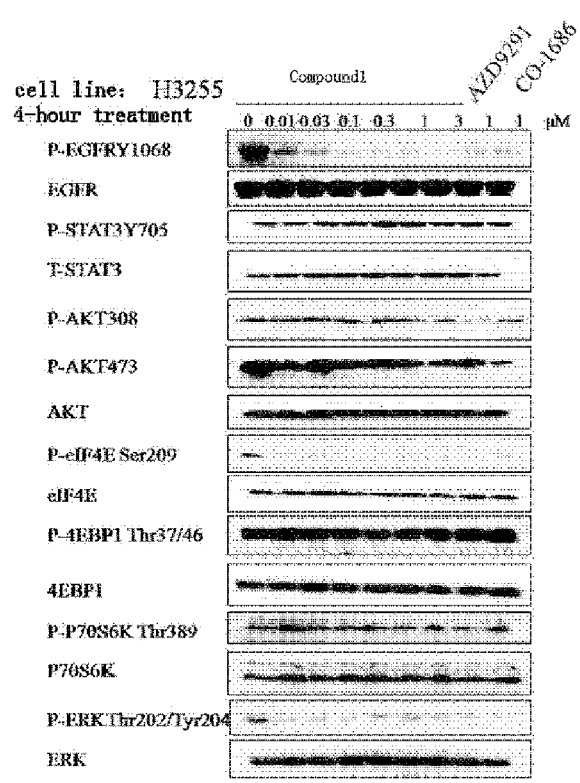
Figure 1D:
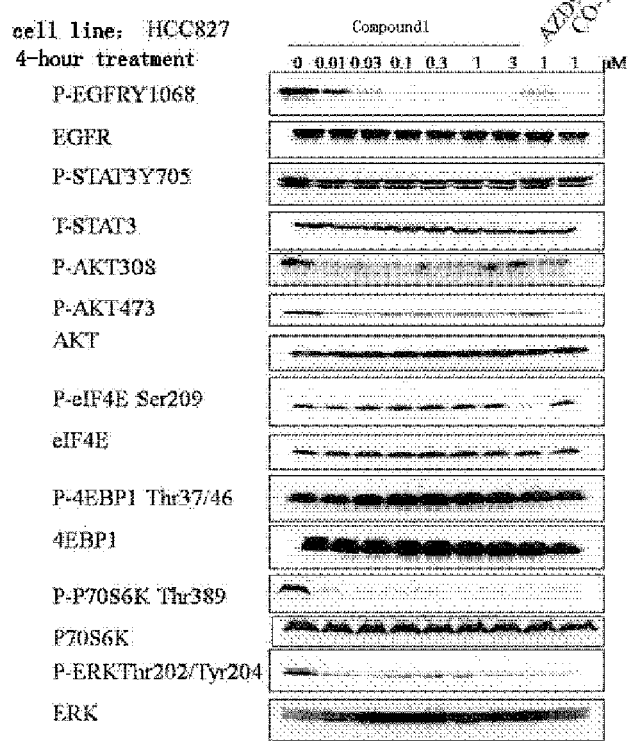
Figure 1E:
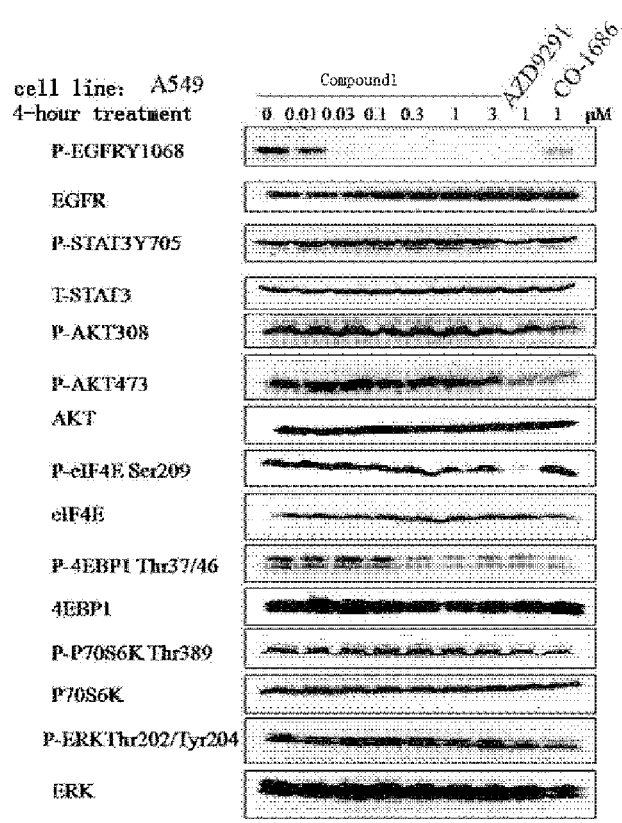
Figure 1F:
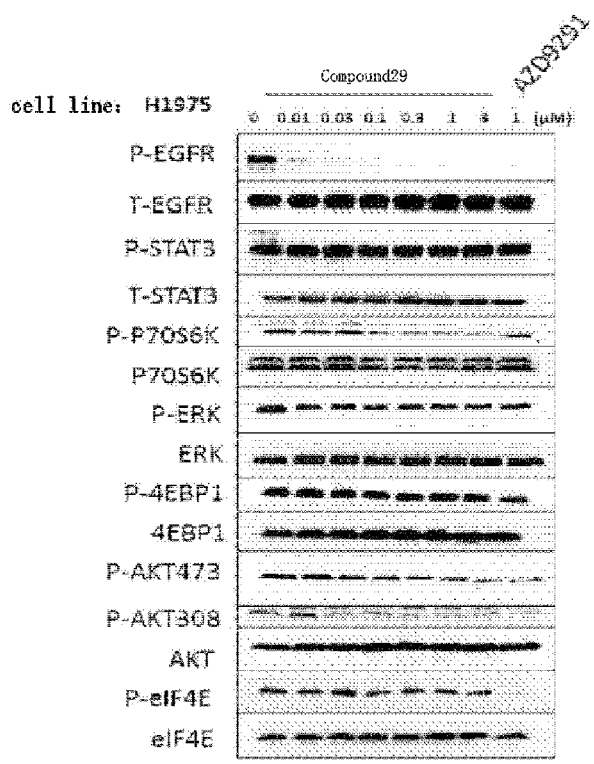
Figure 1G:
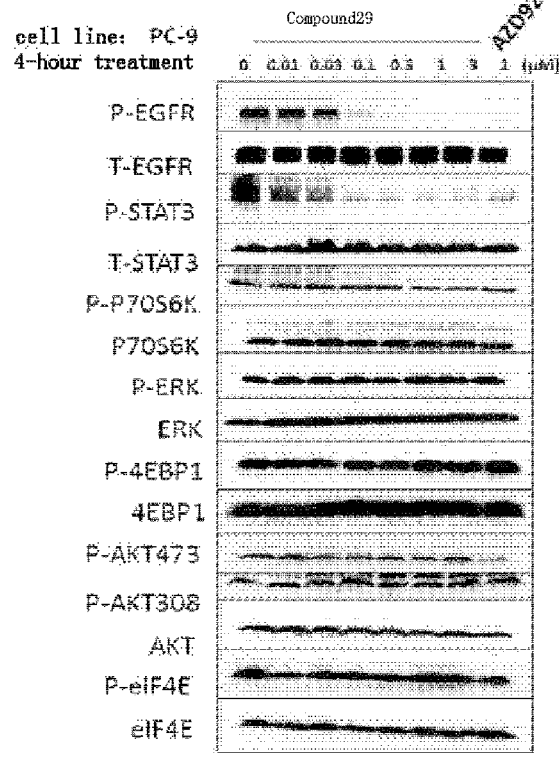
Figure 1H:
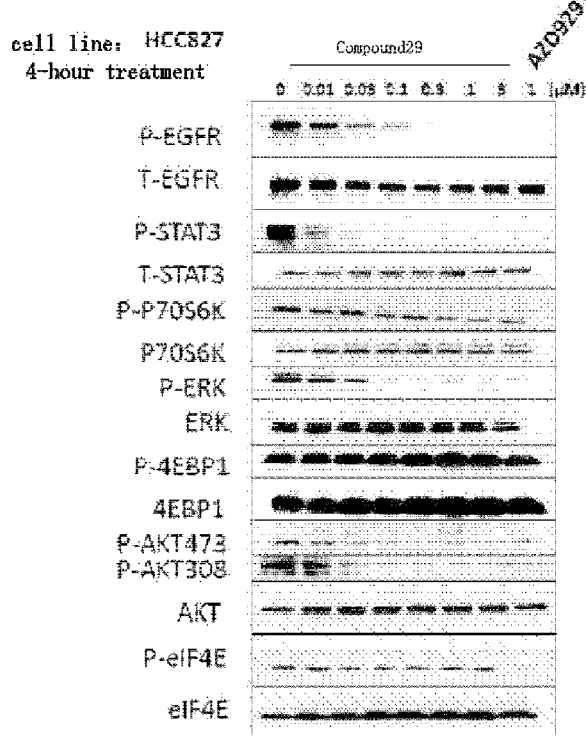
Figure 1I:
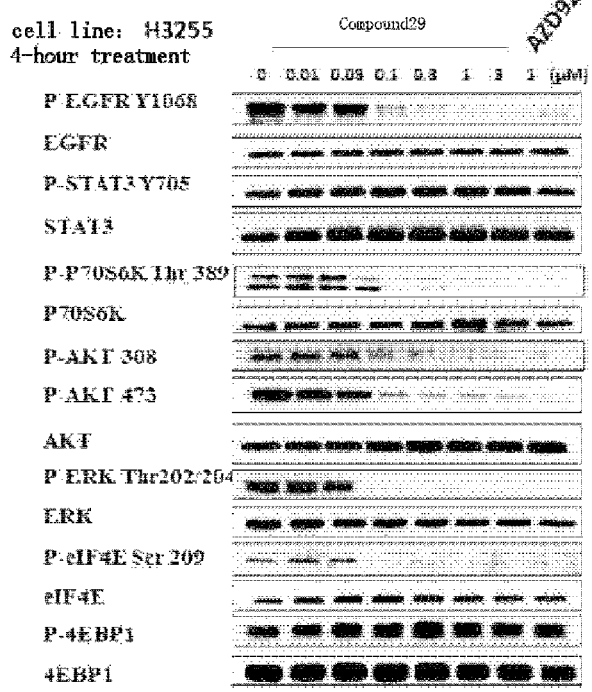
Figure 1J:
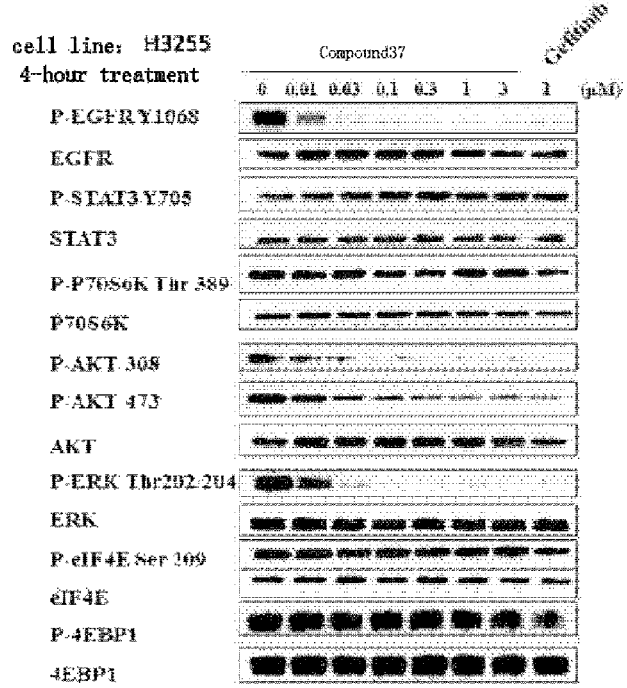

Unless defined otherwise, all technical and scientific terms used herein have the same meaning as is commonly understood by one of skill in the art to which the claimed subject matter belongs.

Unless otherwise indicated, conventional methods of mass spectroscopy, NMR, HPLC, protein chemistry, biochemistry, recombinant DNA techniques and pharmacology that are within the skill of the art are employed in the invention. Unless specific definitions are provided, the nomenclature employed in connection with, and the laboratory procedures and techniques of, analytical chemistry, synthetic organic chemistry, and medicinal and pharmaceutical chemistry described herein are those known in the art. The foregoing techniques and procedures can be generally performed with conventional methods well known in the art and those as described in various general and more specific references that are cited and discussed throughout the present specification.

The term "alkyl" refers to an aliphatic hydrocarbon group, which may be branched or straight. Depending on the structure, an alkyl group may be a monoradical or a diradical (i.e., an alkylene group). In the invention, the alkyl group is preferably a "lower alkyl" having 1 to 8 carbon atoms, more preferably a "lower alkyl" having 1 to 6 carbon atoms, and even more preferably a "lower alkyl" having 1 to 4 carbon atoms. Typical alkyl groups include, but are not limited to, methyl, ethyl, propyl, isopropyl, butyl, isobutyl, tert-butyl, pentyl, hexyl, and the like.

"Alkoxy" refers to a —O-alkyl group, where alkyl is as defined herein. Typical alkoxy groups include, but are not limited to, methoxy, ethoxy, propoxy, butoxy, pentyloxy, hexyloxy, and the like.

The term "aromatic" refers to a planar ring having a delocalized π-electron system containing 4n+2 π electrons, where n is an integer. Aromatic rings can be formed by five, six, seven, eight, nine, or more than nine atoms. Aromatics can be optionally substituted. The term "aromatic" includes both carbocyclic aryl (e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

As used herein, the term "aryl" refers to an aromatic ring wherein each of the atoms forming the ring is a carbon atom. Aryl rings can be formed by five, six, seven, eight, nine, or more than nine carbon atoms. Aryl groups can be optionally substituted. Examples of aryl groups include, but are not limited to phenyl, naphthalenyl, phenanthrenyl, anthracenyl, fluorenyl, and indenyl. Depending on the structure, an aryl group can be a monoradical or a diradical (i.e., an arylene group).

The term "heteroaryl" refers to an aryl group that includes one or more ring heteroatoms selected from nitrogen, oxygen and sulfur. An N-containing "heteroaryl" moiety refers to an aromatic group in which at least one of the skeletal atoms of the ring is a nitrogen atom. Depending on the structure, the heteroaryl group may be a monoradical or a diradical (i.e., a heteroarylene group). Examples of heteroaryl groups include, but are not limited to pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzoindazolyl, indolizinyl, phthalazinyl, pyridazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, naphthyridinyl, furopyridinyl, and the like.

As used herein, the term "heterocycloalkyl" refers to a non-aromatic ring wherein one or more atoms forming the ring is a heteroatom selected from the group consisting of nitrogen, oxygen and sulfur. Heterocycloalkyl rings can be formed by three, four, five, six, seven, eight, nine, or more than nine atoms. Heterocycloalkyl rings can be optionally substituted. Examples of heterocycloalkyls include, but are not limited to, lactams, lactones, cyclic imides, cyclic thioimides, cyclic carbamates, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, imidazolidine, pyrrolidone, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane. Depending on the structure, a heterocycloalkyl group can be a monoradical or a diradical (i.e., a heterocycloalkylene group).

The term "halo" or "halogen" means fluoro, chloro, bromo and iodo.

The terms "haloalkyl" and "haloalkoxy" include alkyl or alkoxy structures in which at least one hydrogen is replaced with a halogen atom. In certain embodiments in which two or more hydrogen atoms are replaced with halogen atoms, the halogen atoms are the same or different as one another.

As used herein, the term "cyano" refers to a group of formula —CN.

The term "optionally substituted" or "substituted" means that the referenced group may be substituted with one or more additional group(s) individually and independently selected from the group consisting of alkyl, cycloalkyl, aryl, heteroaryl, heterocyclyl, hydroxy, alkoxy, cyano, halo, amide, nitro, haloalkyl, amino, methanesulfonyl and the like.

The term "tyrosine protein kinase" (TPK) used herein is a type of kinases that catalyze the transfer of the γ-phosphate from adenosine triphosphate (ATP) to tyrosine residue on proteins and that is capable of catalyzing the phosphorylation of tyrosine residue of various protein substrates, and thus have an important effect in cell growth, proliferation and differentiation.

The terms "inhibits", "inhibiting", or "inhibitor" used in connection with a kinase, as used herein, refer to inhibition of phosphotransferase activity.

A "metabolite" of a compound disclosed herein is a derivative of that compound that is formed when the compound is metabolized. The term "active metabolite" refers to a biologically active derivative of a compound that is formed when the compound is metabolized. The term "metabolized" as used herein, refers to the sum of the processes (including, but not limited to, hydrolysis reactions and reactions catalyzed by enzymes, such as, oxidation reactions) by which a particular substance is changed by an organism. For example, cytochrome P450 catalyzes a variety of oxidative and reductive reactions while uridine diphosphate glucuronyl transferases catalyze the transfer of an activated glucuronic acid molecule to aromatic alcohol, aliphatic alcohol, carboxylic acid, amine and free sulfhydryl group. Further information on metabolism may be obtained from *The Pharmacological Basis of Therapeutics,* 9th Edition, McGraw-Hill (1996). Metabolites of the compounds disclosed herein can be identified either by administration of compounds to a host and analysis of tissue samples from the host, or by incubation of compounds with hepatic cells in vitro and analysis of the resulting compounds. Both methods are well known in the art. In some embodiments, metabolites of a compound are formed by oxidative processes and correspond to the corresponding hydroxy-containing compound. In some embodiments, a compound is metabolized to pharmacologically active metabolites. The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

As used herein, the term "target protein" refers to a protein molecule or a portion of a protein capable of being bound by a selective binding compound. In some embodiments, the target protein is a tyrosine kinase EGFR (wild-type, or various mutants or the combination thereof), ALK (wild-type, or various mutants or the combination thereof), KIT (wild-type, or various mutants or the combination thereof), ABL (wild-type, or various mutants or the combination thereof), FLT3 (wild-type, or various mutants or the combination thereof), BLK (wild-type, or various mutants or the combination thereof), BTK (wild-type, or various mutants or the combination thereof), BMX (wild-type, or various mutants or the combination thereof), VEGFR (wild-type, or various mutants or the combination thereof), RET (wild-type, or various mutants or the combination thereof), PDGFR (wild-type, or various mutants or the combination thereof), MEK (wild-type, or various mutants or the combination thereof), BCR/ABL (wild-type, or various mutants or the combination thereof), JAK (wild-type, or various mutants or the combination thereof), BRAF (wild-type, or various mutants or the combination thereof), MET (wild-type, or various mutants or the combination thereof).

As used herein, $GI_{50}$ refers to a concentration of a medicine required for inhibiting the growth of 50% cells i.e., the medicine concentration at which the growth of 50% cells (such as cancer cells) is inhibited or controlled.

As used herein, $IC_{50}$ refers to an amount, concentration or dosage of a particular test compound that achieves a 50% inhibition of a maximal response, in an assay that measures such response.

Inhibitors of the Present Invention

The present invention relates to a compound of Formula (I) or its pharmaceutically acceptable salts, solvates, isomers, esters, acids, metabolites or prodrugs, said compound having the following structure:

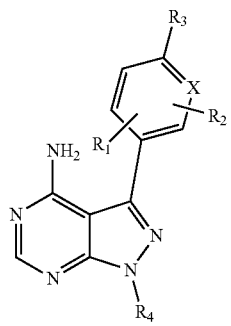

Formula (I)

wherein, X is selected from the group consisting of C and N;

each of $R_1$ and $R_2$ is independently selected from the group consisting of hydrogen, halogen, $C_{1-8}$ alkyl, $C_{1-8}$ haloalkyl, $C_{1-8}$ alkoxy, cyano, and heterocyclylcarbonyl;

$R_3$ is selected from the group consisting of hydrogen, halogen, arylalkoxy, heteroarylalkoxy, heterocyclylalkyl, heterocyclylcarbonyl, or —CO—NH—$(CH_2)_n$-heterocyclyl, wherein n is an integer selected from 0-3, and $R_3$ may be optionally substituted with 1-3 independent $R_6$;

$R_4$ is selected from the group consisting of

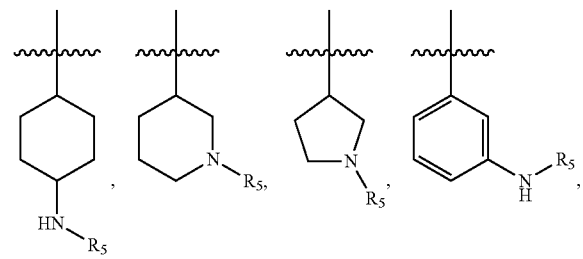

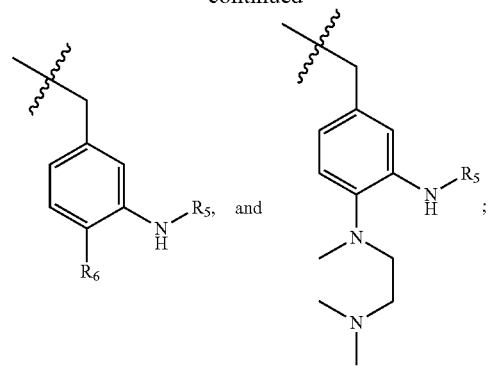

$R_5$ is selected from the group consisting of

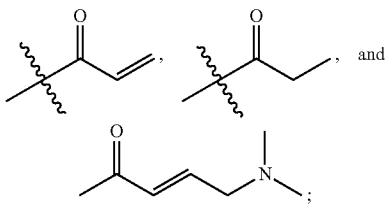

each $R_6$ is independently selected from the group consisting of hydrogen, halogen, $C_{1-8}$ alkyl, $C_{1-8}$ haloalkyl, $C_{1-8}$ alkoxy, cyano, and methanesulfonyl.

Preferably, among the compound of Formula (I) or its pharmaceutically acceptable salts, solvates, isomers, esters, acids, metabolites or prodrugs, each of $R_1$ and $R_2$ is independently selected from the group consisting of hydrogen, fluoro, chloro, methyl, trifluoromethyl, methoxy, cyano, and

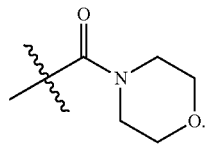 [SMILES: *C(=O)N1CCOCC1]

Further preferably, $R_3$ is selected from the group consisting of: hydrogen; fluoro, chloro; optionally substituted arylmethoxy, such as benzyloxy (especially benzyloxy and m-fluorobenzyloxy, o-fluorobenzyloxy, p-fluorobenzyloxy, 3,4-difluorobenzyloxy, 2,5-difluorobenzyloxy, m-methanesulfonylbenzyloxy); optionally substituted heteroarylmethoxy, such as optionally substituted pyridylmethoxy (especially pyridin-2-ylmethoxy, 6-methylpyridin-2-ylmethoxy, 4-methoxy-3,5-dimethylpyridin-2-ylmethoxy, 6-methyl pyridin-3-ylmethoxy), optionally substituted thienylmethoxy (especially thien-2-ylmethoxy), optionally substituted thiazolylmethoxy (especially thiazol-2-ylmethoxy, (4-methylthiazol-5-yl)methoxy, (2,4-dimethylthiazol-5-yl)methoxy), optionally substituted furylmethoxy (especially furan-2-ylmethoxy), optionally substituted isoxazolylmethoxy (especially 5-methylisoxazol-3-ylmethoxy), optionally substituted indolylmethoxy (especially indol-3-ylmethoxy, N-methyl indol-3-ylmethoxy), optionally substituted imidazolylmethoxy (especially imidazol-2-ylmethoxy, (1-methyl-1H-imidazol-2-yl)methoxy), optionally substituted indazolylmethoxy (especially indazol-3-ylmethoxy, (1-methyl-1H-indazol-3-yl)methoxy), optionally substituted pyrazolylmethoxy (especially (3,5-dimethyl-1H-pyrazol-1-yl)methoxy, (1,3-dimethyl-1H-pyrazol-5-yl)methoxy); optionally substituted piperazinylmethyl (especially N-methyl-piperazinyl-N-methyl); optionally substituted morpholinylcarbonyl (especially morpholin-4-ylcarbonyl); and optionally substituted —CO—NH—$(CH_2)_n$-morpholinyl (especially —CO—NH-morpholinyl, —CO—NH—$(CH_2)_2$-morpholinyl).

More preferably, X is C, one of $R_1$ and $R_2$ is hydrogen and the other is chloro, and the chloro substituent is replaced at X.

Still preferably, $R_3$ is selected from the group consisting of m-fluorobenzyloxy, pyridin-2-ylmethoxy, and 6-methylpyridin-2-ylmethoxy.

Further preferably, $R_4$ is selected from the group consisting of

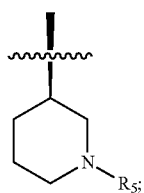

and $R_5$ is selected from the group consisting of

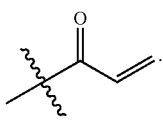 [SMILES: *C(=O)C=C]

In a further embodiment, the present application provides a compound of Formula (II) or its pharmaceutically acceptable salts, solvates, isomers, esters, acids, metabolites or prodrugs:

Formula (II)

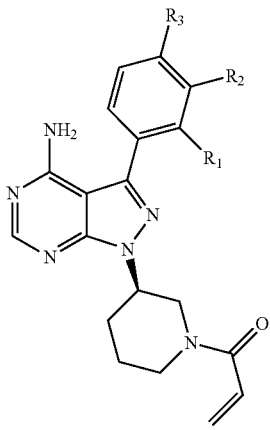

wherein, each of $R_1$ and $R_2$ is independently selected from the group consisting of hydrogen, halogen, $C_{1-8}$ alkyl, $C_{1-8}$ haloalkyl, $C_{1-8}$ alkoxy, and cyano;
$R_3$ is selected from the group consisting of halo, arylalkoxy, and heteroarylalkoxy, and $R_3$ may be optionally substituted with 1-3 independent $R_6$;

each $R_6$ is independently selected from the group consisting of hydrogen, halogen, $C_{1-8}$ alkyl, and $C_{1-8}$ alkoxy.

Preferably, in the compound of Formula (II) or its pharmaceutically acceptable salts, solvates, isomers, esters, acids, metabolites or prodrugs, each of $R_1$ and $R_2$ is independently selected from the group consisting of hydrogen, fluoro, chloro, methyl, trifluoromethyl, methoxy, and cyano. More preferably, $R_1$ is hydrogen, and $R_2$ is chloro.

Further preferably, $R_3$ is selected from the group consisting of: fluoro, chloro; optionally substituted arylmethoxy, such as benzyloxy (especially benzyloxy and m-fluorobenzyloxy, o-fluorobenzyloxy, p-fluorobenzyloxy, 3,4-difluorobenzyloxy, 2,5-difluorobenzyloxy); optionally substituted heteroarylmethoxy, such as optionally substituted pyridylmethoxy (especially pyridin-2-ylmethoxy, 6-methyl pyridin-2-ylmethoxy, 4-methoxy-3,5-dimethylpyridin-2-ylmethoxy, 6-methylpyridin-3-ylmethoxy), optionally substituted thiazolyl methoxy (especially thiazol-2-ylmethoxy), optionally substituted imidazolylmethoxy (especially imidazol-2-ylmethoxy, (1-methyl-1H-imidazol-2-yl)methoxy). More preferably, $R_3$ is selected from the group consisting of m-fluorobenzyloxy, pyridin-2-ylmethoxy, and 6-methyl pyridin-2-yl methoxy.

The chiral compounds involved in the present invention may be of any configuration or may be mixed racemates.

Described herein are novel kinase inhibitors. The pharmaceutically acceptable salts, solvates, esters, acids, pharmaceutically active metabolites and prodrugs of these compounds are also described herein.

In additional or in further embodiments, the compounds described herein are metabolized upon administration to an organism in need to produce a metabolite that is then used to produce a desired effect, including a desired therapeutic effect.

Compounds described herein may be formed as, and/or used as, pharmaceutically acceptable salts. The type of pharmaceutical acceptable salts, include, but are not limited to: (1) acid-addition salts, formed by reacting the free base form of the compound with a pharmaceutically acceptable inorganic acid such as hydrochloric acid, hydrobromic acid, sulfuric acid, nitric acid, phosphoric acid, metaphosphoric acid, and the like; or with an organic acid such as acetic acid, propionic acid, hexanoic acid, cyclopentanepropionic acid, glycolic acid, pyruvic acid, lactic acid, malonic acid, malic acid, citric acid, succinic acid, maleic acid, tartaric acid, fumaric acid, trifluoroacetic acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 4-methylbicyclo-[2.2.2]oct-2-ene-1-carboxylic acid, 2-naphthalenesulfonic acid, tert-butylacetic acid, glucoheptonic acid, 4,4'-methylenebis-(3-hydroxy-2-ene-1-carboxylic acid), 3-phenylpropionic acid, trimethylacetic acid, lauryl sulfuric acid, gluconic acid, glutamic acid, salicylic acid, hydroxynaphthoic acid, stearic acid, muconic acid, and the like; (2) base-addition salts formed when an acidic proton present in the parent compound either is replaced by a metal ion, e.g., an alkali metal ion (e.g. lithium, sodium, potassium), an alkaline earth ion (e.g. magnesium, or calcium), or an aluminum ion; or coordinates with an organic base. Acceptable organic bases include ethanolamine, diethanolamine, triethanolamine, trimethylamine, N-methylglucamine, and the like. Acceptable inorganic bases include aluminum hydroxide, calcium hydroxide, potassium hydroxide, sodium carbonate, sodium hydroxide, and the like.

The corresponding counterions of the pharmaceutically acceptable salts may be analyzed and identified using various methods including, but not limited to, ion exchange chromatography, ion chromatography, capillary electrophoresis, inductively coupled plasma, atomic absorption spectroscopy, mass spectrometry, or any combination thereof.

The salts are recovered by using at least one of the following techniques: filtration, precipitation with a non-solvent followed by filtration, evaporation of the solvent, or, in the case of aqueous solutions, lyophilization.

The screening and characterization of the pharmaceutically acceptable salts, polymorphs and/or solvates may be accomplished using a variety of techniques including, but not limited to, thermal analysis, x-ray diffraction, spectroscopy, microscopy, and elemental analysis. The various spectroscopic techniques used include, but are not limited to, Raman, FTIR, UVIS, and NMR (liquid and solid state). The various microscopy techniques include, but are not limited to, IR microscopy and Raman microscopy.

Pharmaceutical Composition of the Present Invention

The present application also provides a pharmaceutical composition which comprises the compound of Formula (I) or Formula (II) or its pharmaceutically acceptable salts, solvates, esters, acids, active metabolites of drugs, or prodrugs, and pharmaceutically acceptable carrier or excipient, as well as optionally other therapeutic agents.

The medicament comprising a compound of the invention may be used singly or in combination with one or more other therapeutic agents during treatment as required. The medicament comprising a compound of the invention may be administered to a patient through at least one of injection, oral administration, inhalation, rectal and transdermal administration.

In the embodiments of the invention, when a patient is treated in accordance with the invention, the amount of a given agent will vary depending upon factors such as the particular dosing regimen, the type of the disease or condition and its severity, the identity (e.g., weight) of the subject or host in need of treatment, but can be routinely determined in a manner known in the art according to the particular circumstances surrounding the case, including, e.g., the specific agent being administered, the route of administration, the condition being treated, and the subject or host being treated. In general, doses employed for adult human treatment will typically be in the range of 0.02-5000 mg per day, such as from about 1-1500 mg per day. The desired dose may conveniently be presented in a single dose or as divided doses administered simultaneously (or over a short period of time) or at appropriate intervals, for example as two, three, four or more sub-doses per day. It will be appreciated by those skilled in the art that, although the above dosage ranges are given, the specific effective amounts may be appropriately adjusted depending on the condition of the patient and the judgment of the practitioner.

Use of Medicines of the Present Invention

The compound of Formula (I) or Formula (II), or the pharmaceutically acceptable salts, solvates, esters, acids, metabolites or prodrugs thereof, or the pharmaceutical compound comprising the same may be used for inhibiting the activity of one or more substances selected from the group consisting of: tyrosine kinase EGFR (wild-type, or various mutants or the combination thereof), ALK (wild-type, or various mutants or the combination thereof), KIT (wild-type, or various mutants or the combination thereof), ABL (wild-type, or various mutants or the combination thereof), FLT3 (wild-type, or various mutants or the combination thereof), BLK (wild-type, or various mutants or the combination thereof), BTK (wild-type, or various mutants or the combination thereof), BMX (wild-type, or various mutants or the combination thereof), VEGFR (wild-type, or various mutants or the combination thereof), RET (wild-type, or various mutants or the combination thereof), PDGFR (wild-type, or various mutants or the combination thereof), MEK (wild-type, or various mutants or the combination thereof), BCR/ABL (wild-type, or various mutants or the combination thereof), JAK (wild-type, or various mutants or the combination thereof), BRAF (wild-type, or various mutants or the combination thereof), MET (wild-type, or various mutants or the combination thereof). The compound of Formula (I) or Formula (II) or the pharmaceutically acceptable salts, solvates, esters, acids, metabolites or prodrugs thereof together with a pharmaceutically acceptable carrier or excipient may be used for treating a disease selected from the group consisting of or may be used for preparation of a medicament for treating a disease selected from the group consisting of: non-small cell lung cancer, small cell lung cancer, lung adenocarcinoma, lung squamous carcinoma, pancreatic cancer, prostate cancer, bladder cancer, liver cancer, skin cancer, glioma, breast cancer, melanoma, glioblastoma, rhabdomyosarcoma, ovarian cancer, astrocytoma, Ewing's sarcoma, retinoblastoma, epithelial cell carcinoma, colon cancer, kidney cancer, gastrointestinal stromal tumor, leukemia, histiocytic lymphoma, and nasopharyngeal carcinoma.

The compound of Formula (I) or Formula (II), or the pharmaceutically acceptable salts, solvates, esters, acids, metabolites or prodrugs thereof, or the pharmaceutical composition comprising the same are particularly suitable for treating non-small cell lung cancer, especially drug-resistant non-small cell lung cancer with wild-type EGFR and/or EGFR T790M mutation and/or EGFR L858R mutation and/or EGFR delE746_A750 mutation.

Preparation of the Compounds

Compounds of Formula (I), or (II) may be synthesized using standard synthetic techniques known to those of skill in the art or using methods known in the art in combination with methods described herein. In additions, solvents, temperatures and other reaction conditions presented herein may be modified according to those of skill in the art. As a further guide, the following synthetic method may also be used.

The reactions may be carried out orderly to provide the compound described herein; or they can be carried out to synthesize fragments which are subsequently incorporated according to methods described herein and/or methods known in the art.

In certain embodiments, provided herein are methods of making and methods of using tyrosine kinase inhibitor compounds described herein. In certain embodiments, compounds described herein can be synthesized using the following synthetic schemes. Compounds may be synthesized using methodologies analogous to those described below by the use of appropriate alternative starting materials.

The starring materials used for the synthesis of the compounds described herein may be synthesized or can be obtained from commercial sources. The compounds described herein and other related compounds having different substituents can be synthesized using techniques and materials known to those of skill in the art. General methods for the preparation of compounds as disclosed herein may be derived from reactions known in the art and the reactions may be modified by use of appropriate reagents and conditions, as would be recognized by the skilled person, for the introduction of the various moieties into the molecules as provided herein.

The products of the reactions may be isolated and purified, if desired, using conventional techniques, including, but not limited to, filtration, distillation, crystallization, chromatography and the like. Such products may be characterized using conventional means, including physical constants and spectral data.

EXAMPLES

The following specific and non-limiting examples are to be construed as merely illustrative, and do not limit the present disclosure in any way whatsoever. Without further elaboration, it is believed that one skilled in the art can, based on the description herein, utilize the present disclosure to its fullest extent.

Synthesis of compounds of the present invention and the intermediates

Example 1

Synthesis of Compound 1 (R)-1-(3-(4-amino-3-(3-chloro-4-(pyridin-2-ylmethoxy)phenyl)-1H-pyrazolo[3,4-d]pyrimidin-1-yl)piperidin-1-yl)prop-2-en-1-one

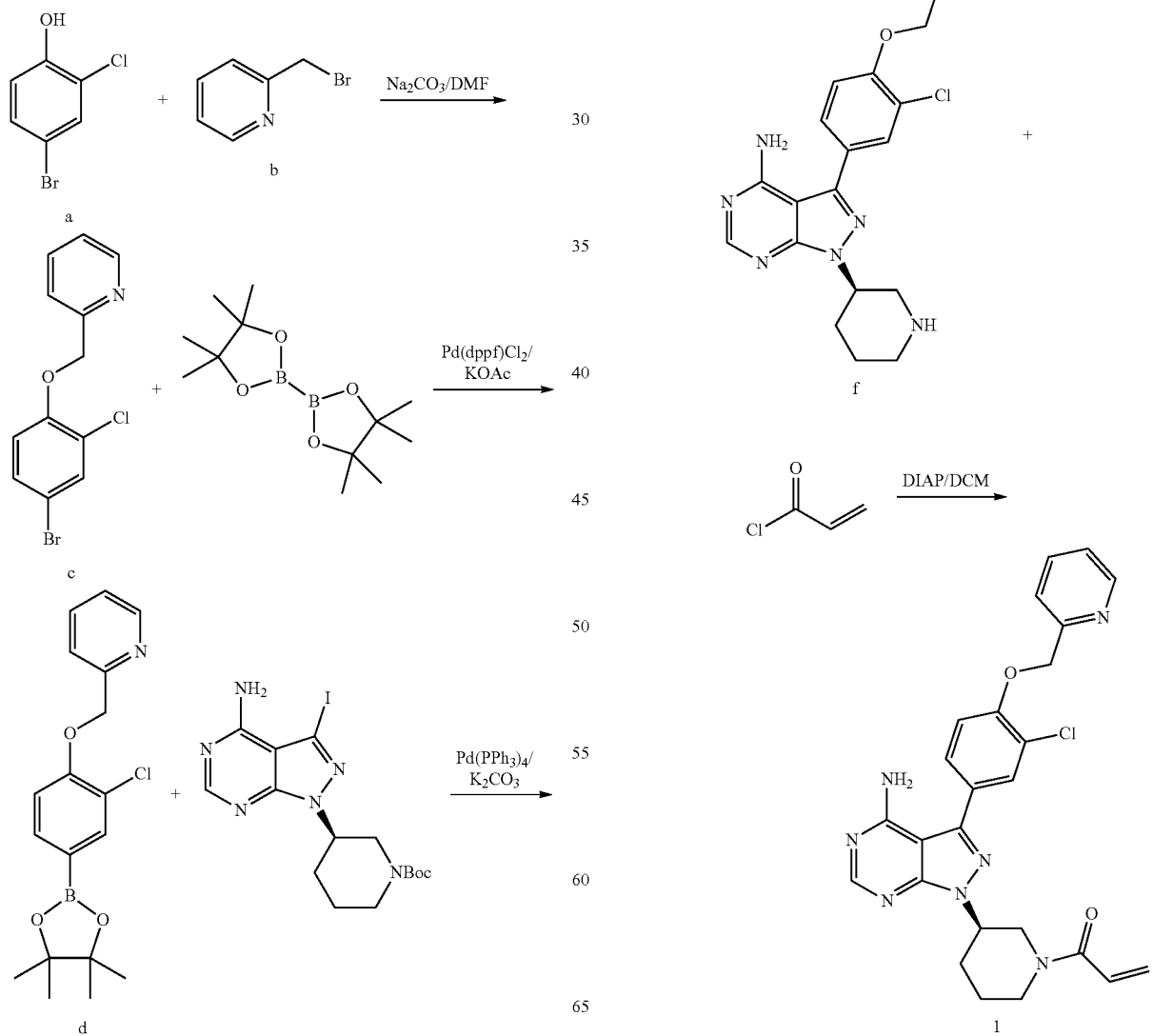

-continued

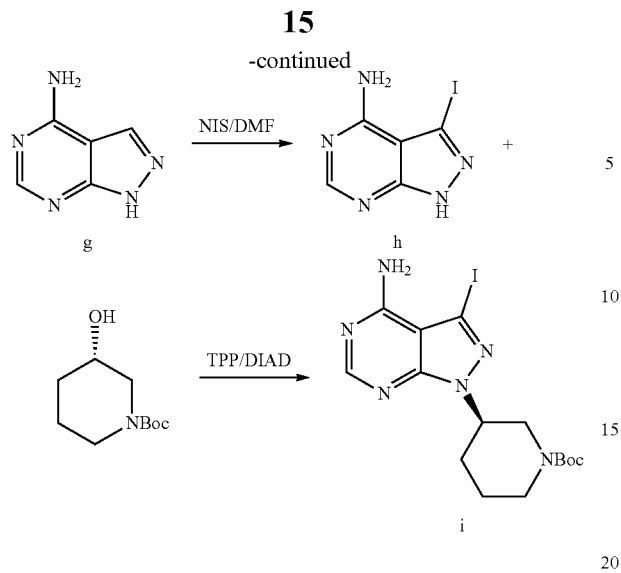

Step 1: Synthesis of Compound c

Compound a 2-chloro-4-bromophenol (2 g, 1 eq), Compound b 2-(bromomethyl)pyridine (0.83 g, 1 eq) and Na$_2$CO$_3$ (4 g, 2 eq) were mixed and added into N,N-dimethylformamide (DMF), and stirred at 50° C. for 5 h. After cooling, the mixture was diluted with ethyl acetate, washed with water three times and then with saturated NaCl solution, and further concentrated. The resultant was used directly for subsequent steps.

Step 2: Synthesis of Compound d

Compound c (2 g, 1 eq), bis(pinacolato)diboron (2 g, 1.2 eq), potassium acetate (KOAc) (1.3 g, 2 eq) and Pd(dppf)Cl$_2$ (0.27 g, 0.02 eq) were mixed and added with 1,4-dioxane, stirred overnight under nitrogen at 100° C., and then subjected to concentration and column chromatography, giving 1.5 g of solid.

Step 3: Synthesis of Compound h

Compound g (10, 1 eq), NIS (25 g, 2.5 eq) and N,N-dimethylformamide (DMF) (100 mL) were mixed and stirred overnight under nitrogen at 80° C., and then cooled and poured into water (500 mL). Solids were filtered out and washed successively with saturated sodium bisulfite (50 mL) and water (100 mL), and then dried under vacuum for 10 h at 50° C., giving 16 g of solid.

Step 4: Synthesis of Compound i

Compound triphenylphosphine (7 g, 3.5 eq) and THF (100 mL) were mixed and to the mixture diisopropyl azodicarboxylate (DIAD) (5 mL, 3.5 eq) was added dropwise under the protection of nitrogen at 0° C., followed by addition of (S)-1-(tert-butoxycarbonyl)-3-hydroxypiperidine (3 g, 2 eq), Compound h (1 g, 1 eq). The resultant was stirred at room temperature overnight, and then subjected to concentration and column chromatography, giving 1.5 g of solid.

Step 5: Synthesis of Compound e

Compound d (0.9 g, 1.2 eq), Compound i (0.1 g, 1 eq), Pd(PPh$_3$)$_4$ (0.013 g, 0.05 eq), K$_2$CO$_3$ (0.062 g, 2 eq), 1,4-dioxane/H$_2$O (12 mL, 5/1) were mixed and stirred overnight under nitrogen at 100° C., followed by concentration and direct column chromatography, giving 0.1 g of solid.

Step 6: Synthesis of Compound f

Compound e (0.1 g, 1 eq) was dissolved in ethyl acetate (1 mL), added with 4N HCl in ethyl acetate (5 mL), stirred 0.5 h at room temperature and then concentrated to obtain 0.12 g of solid.

Step 7: Synthesis of Compound 1, (R)-1-(3-(4-amino-3-(3-chloro-4-(pyridin-2-ylmethoxy)phenyl)-1H-pyrazolo[3,4-d]pyrimidin-1-yl)piperidin-1-yl)prop-2-en-1-one Compound f (0.12 g, 1 eq), diisoamyl phosphate (DIAP) (0.17 g, 5 eq), DCM were mixed and acryloyl chloride (0.027 g, 1.1 ed) was added dropwise in an ice bath. At the completion of dropping, the reaction was quenched with methanol, and the resultant was concentrated and subjected to column chromatography to obtain 0.03 g of solid.

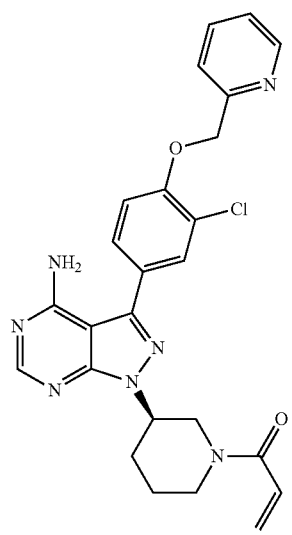 [SMILES: C=CC(=O)N1CCC[C@@H](n2nc(-c3ccc(OCc4ccccn4)c(Cl)c3)c3c(N)ncnc32)C1]

Exact Mass (calculated): 489.17; MS(ESI) m/z(M+1)$^+$: 490.1722.

Example 2

Synthesis of Compound 2 (R)-1-(3-(4-amino-3-(3-chloro-4-((3-fluorobenzyl)oxy)phenyl)-1H-pyrazolo[3,4-d]pyrimidin-1-yl)piperidin-1-yl)prop-2-en-1-one

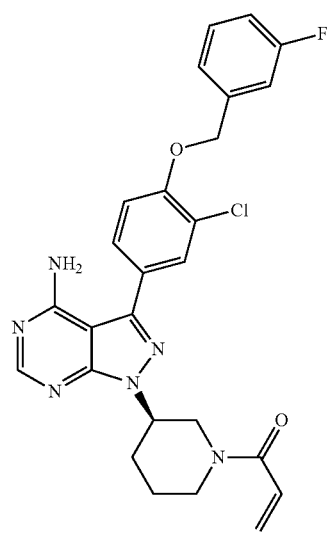

Synthesis of Compound 2 was completed by using steps similar to those described in Example 1. Exact Mass (calculated): 506.16; MS(ESI) m/z(M+1)$^+$: 507.1758.

Example 3

Synthesis of Compound 3 N-(4-amino-3-(3-chloro-4-((3-fluorobenzyl)oxy)phenyl)-1H-pyrazolo[3,4-d]pyrimidin-1-yl)cyclohexyl) acrylamide

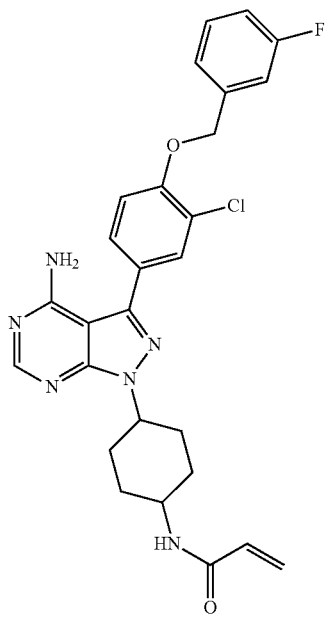 [SMILES: C=CC(=O)NC1CCC(n2nc(-c3ccc(OCc4cccc(F)c4)c(Cl)c3)c3c(N)ncnc32)CC1]

Synthesis of Compound 3 was completed by using steps similar to those described in Example 1. Exact Mass (calculated): 520.18; MS(ESI) m/z(M+1)$^+$: 521.1878.

Example 4

Synthesis of Compound 4 (R)-1-(3-(4-amino-3-(3-chloro-4-((3-fluorobenzyl)oxy)phenyl)-1H-pyrazolo[3,4-d]pyrimidin-1-yl)pyrrolidin-1-yl)prop-2-en-1-one

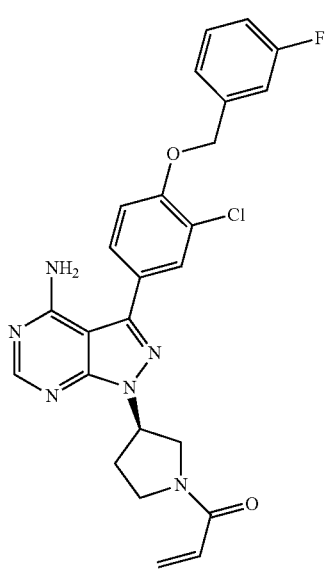 [SMILES: C=CC(=O)N1CC[C@@H](n2nc(-c3ccc(OCc4cccc(F)c4)c(Cl)c3)c3c(N)ncnc32)C1]

Synthesis of Compound 4 was completed by using steps similar to those described in Example 1. Exact Mass (calculated): 492.15; MS(ESI) m/z(M+1)$^+$: 493.1575.

Example 5

Synthesis of Compound 5 (R)-1-(3-(4-amino-3-(3-chloro-4-(pyridin-2-ylmethoxy)phenyl)-1H-pyrazolo[3,4-d]pyrimidin-1-yl)pyrrolidin-1-yl)prop-2-en-1-one

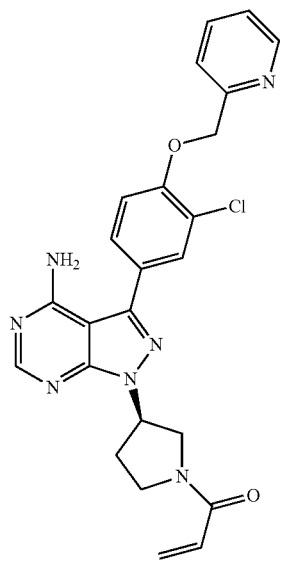 [SMILES: C=CC(=O)N1CC[C@@H](n2nc(-c3ccc(OCc4ccccn4)c(Cl)c3)c3c(N)ncnc32)C1]

Synthesis of Compound 5 was completed by using steps similar to those described in Example 1. Exact Mass (calculated): 475.15; MS(ESI) m/z(M+1)$^+$: 476.1685.

Example 6

Synthesis of Compound 6 (R,E)-1-(3-(4-amino-3-(3-chloro-4-(pyridin-2-ylmethoxy)phenyl)-1H-pyrazolo[3,4-d]pyrimidin-1-yl)piperidin-1-yl)-4-(dimethylamino)but-2-en-1-one

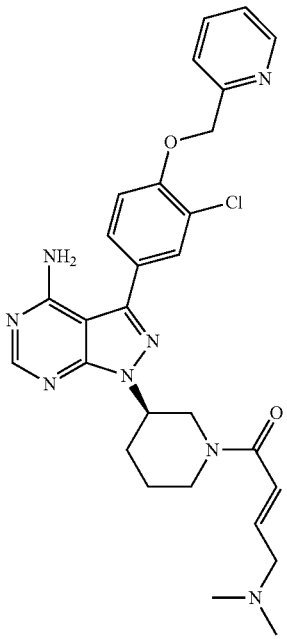 [SMILES: CN(C)C/C=C/C(=O)N1CCC[C@@H](n2nc(-c3ccc(OCc4ccccn4)c(Cl)c3)c3c(N)ncnc32)C1]

Synthesis of Compound 6 was completed by using steps similar to those described in Example 1. Exact Mass (calculated): 546.23; MS(ESI) m/z(M+1)⁺: 547.2335.

Example 7

Synthesis of Compound 7 (R)-1-(3-(4-amino-3-(4-(benzyloxy)phenyl)-1H-pyrazolo[3,4-d]pyrimidin-1-yl)piperidin-1-yl)prop-2-en-1-one

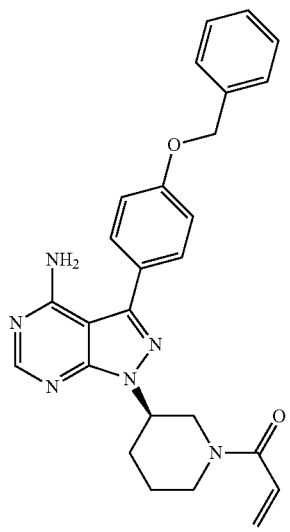 [SMILES: C=CC(=O)N1CCC[C@@H](n2nc(-c3ccc(OCc4ccccc4)cc3)c3c(N)ncnc32)C1]

Synthesis of Compound 7 was completed by using steps similar to those described in Example 1. Exact Mass (calculated): 454.21; MS(ESI) m/z(M+1)⁺: 456.2246.

Example 8

Synthesis of Compound 8 (R)-1-(3-(4-amino-3-(3-chloro-4-((3-fluorobenz yl)oxy)-3-methoxyphenyl)-1H-pyrazolo[3,4-d]pyrimidin-1-yl)piperidin-1-yl)prop-2-en-1-one

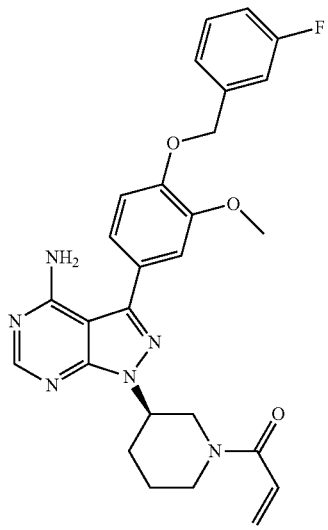 [SMILES: C=CC(=O)N1CCC[C@@H](n2nc(-c3ccc(OCc4cccc(F)c4)c(OC)c3)c3c(N)ncnc32)C1]

Synthesis of Compound 8 was completed by using steps similar to those described in Example 1. Exact Mass (calculated): 502.21; MS(ESI) m/z(M+1)⁺: 503.2236.

Example 9

Synthesis of Compound 9 (R)-1-(3-(4-amino-3-(3-methyl-4-(pyridin-2-ylmethoxy)phenyl)-1H-pyrazolo[3,4-d]pyrimidin-1-yl)piperidin-1-yl)prop-2-en-1-one

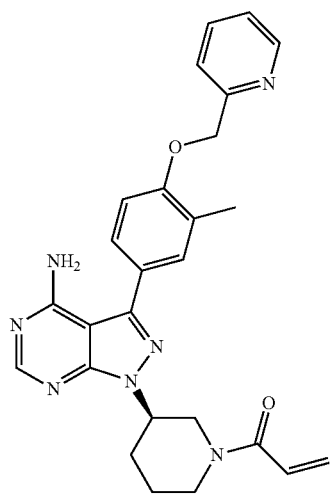 [SMILES: C=CC(=O)N1CCC[C@@H](n2nc(-c3ccc(OCc4ccccn4)c(C)c3)c3c(N)ncnc32)C1]

Synthesis of Compound 9 was completed by using steps similar to those described in Example 1. Exact Mass (calculated): 466.22; MS(ESI) m/z(M+1)⁺: 470.2326.

Example 10

Synthesis of Compound 10 (R)-1-(3-(4-amino-3-(3-methoxy-4-(pyridin-2-ylmethoxy)phenyl)-1H-pyrazolo[3,4-d]pyrimidin-1-yl)piperidin-1-yl)prop-2-en-1-one

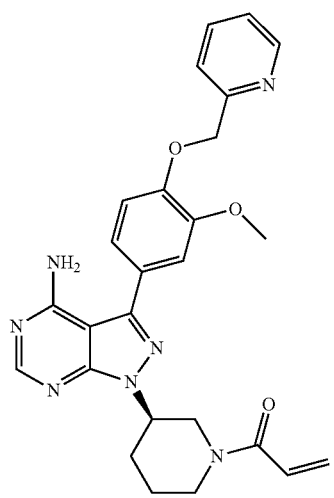 [SMILES: C=CC(=O)N1CCC[C@@H](n2nc(-c3ccc(OCc4ccccn4)c(OC)c3)c3c(N)ncnc32)C1]

Synthesis of Compound 10 was completed by using steps similar to those described in Example 1. Exact Mass (calculated): 485.22; MS(ESI) m/z(M+1)$^+$: 486.2214.

Example 11

Synthesis of Compound 11 (R)-1-(3-(4-amino-3-(3-cyano-4-(pyridin-2-ylmethoxy)phenyl)-1H-pyrazolo[3,4-d]pyrimidin-1-yl)piperidin-1-yl)prop-2-en-1-one

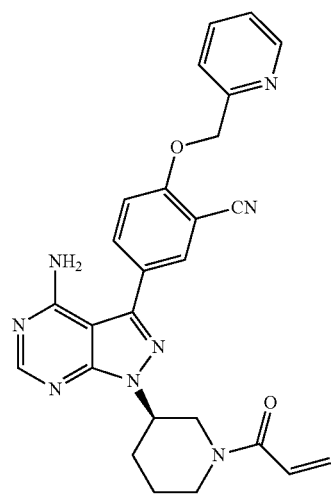 [SMILES: C=CC(=O)N1CCC[C@@H](n2nc(-c3ccc(OCc4ccccn4)c(C#N)c3)c3c(N)ncnc32)C1]

Synthesis of Compound 11 was completed by using steps similar to those described in Example 1. Exact Mass (calculated): 480.20; MS(ESI) m/z(M+1)$^+$: 481.2113.

Example 12

Synthesis of Compound 12 (R)-1-(3-(4-amino-3-(4-(benzyloxy)-3-fluorophenyl)-1H-pyrazolo[3,4-d]pyrimidin-1-yl)piperidin-1-yl)prop-2-en-1-one

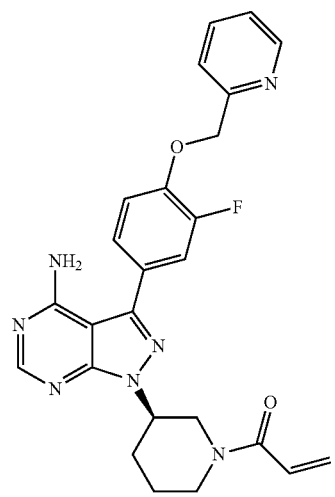

Synthesis of Compound 12 was completed by using steps similar to those described in Example 1. Exact Mass (calculated): 472.20; MS(ESI) m/z(M+1)$^+$: 473.2112.

Example 13

Synthesis of Compound 13 (R)-1-(3-(4-amino-3-(3-fluoro-4-((3-fluorobenzyl)oxy)phenyl)-1H-pyrazolo[3,4-d]pyrimidin-1-yl)piperidin-1-yl)prop-2-en-1-one

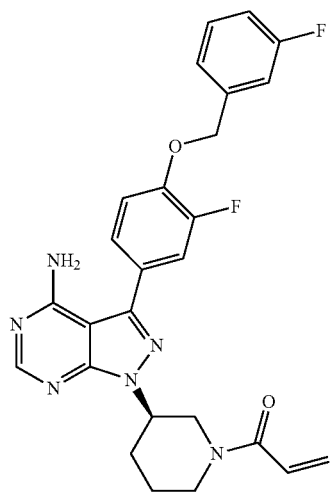

Synthesis of Compound 13 was completed by using steps similar to those described in Example 1. Exact Mass (calculated): 490.19; MS(ESI) m/z(M+1)$^+$: 491.2011.

Example 14

Synthesis of Compound 14 (R)-1-(3-(4-amino-3-(3-methyl-4-((3-fluorobenzyl)oxy)phenyl)-1H-pyrazolo[3,4-d]pyrimidin-1-yl)piperidin-1-yl)prop-2-en-1-one

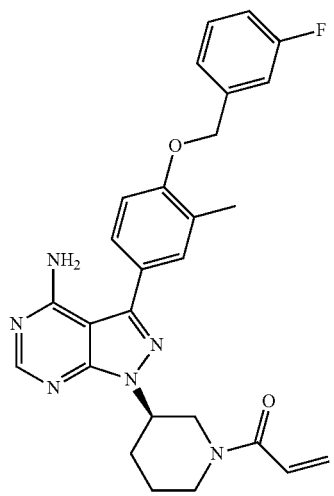 [SMILES: C=CC(=O)N1CCC[C@@H](n2nc(-c3ccc(OCc4cccc(F)c4)c(C)c3)c3c(N)ncnc32)C1]

Synthesis of Compound 14 was completed by using steps similar to those described in Example 1. Exact Mass (calculated): 486.22; MS(ESI) m/z(M+1)$^+$: 487.2231.

Example 15

Synthesis of Compound 15 (R)-1-(3-(4-amino-3-(4-(benzyloxy)-3-chlorophenyl)-1H-pyrazolo[3,4-d]pyrimidin-1-yl)piperidin-1-yl)prop-2-en-1-one

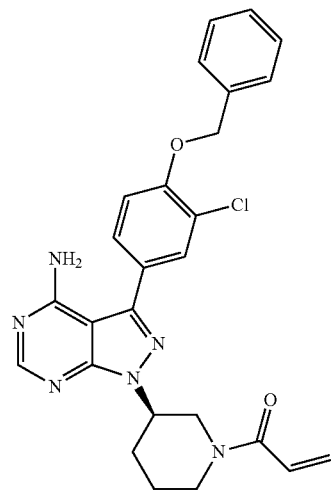 [SMILES: C=CC(=O)N1CCC[C@@H](n2nc(-c3ccc(OCc4ccccc4)c(Cl)c3)c3c(N)ncnc32)C1]

Synthesis of Compound 15 was completed by using steps similar to those described in Example 1. Exact Mass (calculated): 488.17; MS(ESI) m/z(M+1)$^+$: 489.1816.

Example 16

Synthesis of Compound 16 (R)-1-(3-(4-amino-3-(3-cyano-4-((3-fluorobenzyl)oxy)phenyl)-1H-pyrazolo[3,4-d]pyrimidin-1-yl)piperidin-1-yl)prop-2-en-1-one

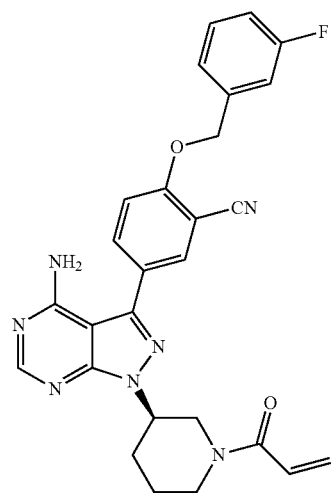 [SMILES: C=CC(=O)N1CCC[C@@H](n2nc(-c3ccc(OCc4cccc(F)c4)c(C#N)c3)c3c(N)ncnc32)C1]

Synthesis of Compound 16 was completed by using steps similar to those described in Example 1. Exact Mass (calculated): 497.20; MS(ESI) m/z(M+1)$^+$: 498.2018.

Example 17

Synthesis of Compound 17 (R)-1-(3-(4-amino-3-(3-fluoro-4-(pyridin-2-ylmethoxy)phenyl)-1H-pyrazolo[3,4-d]pyrimidin-1-yl)piperidin-1-yl)prop-2-en-1-one

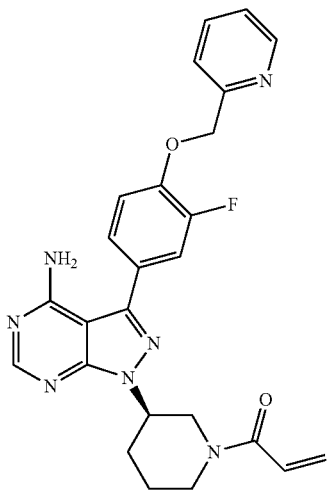 [SMILES: C=CC(=O)N1CCC[C@@H](n2nc(-c3ccc(OCc4ccccn4)c(F)c3)c3c(N)ncnc32)C1]

Synthesis of Compound 17 was completed by using steps similar to those described in Example 1. Exact Mass (calculated): 473.20; MS(ESI) m/z(M+1)$^+$: 474.2017.

Example 18

Synthesis of Compound 18 (R)-1-(3-(4-amino-3-(3-chloro-4-((2-fluorobenzyl)oxy)phenyl)-1H-pyrazolo[3,4-d]pyrimidin-1-yl)piperidin-1-yl)prop-2-en-1-one

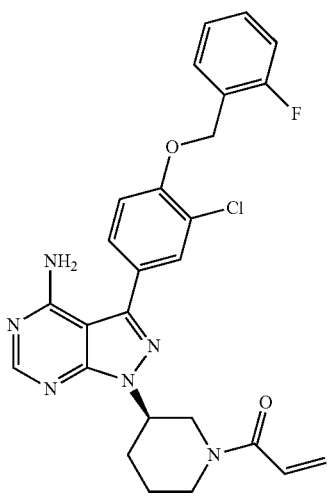 [SMILES: C=CC(=O)N1CCC[C@@H](n2nc(-c3ccc(OCc4ccccc4F)c(Cl)c3)c3c(N)ncnc32)C1]

Synthesis of Compound 18 was completed by using steps similar to those described in Example 1. Exact Mass (calculated): 506.16; MS(ESI) m/z(M+1)$^+$: 507.1711.

Example 19

Synthesis of Compound 19 (R)-1-(3-(4-amino-3-(6-((3-fluorobenzyl)oxy)pyridin-3-yl)-1H-pyrazolo[3,4-d]pyrimidin-1-yl)piperidin-1-yl)prop-2-en-1-one

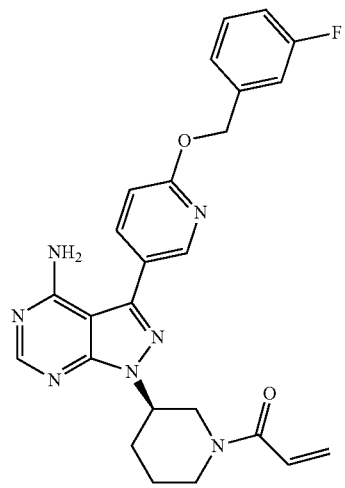 [SMILES: C=CC(=O)N1CCC[C@@H](n2nc(-c3ccc(OCc4cccc(F)c4)nc3)c3c(N)ncnc32)C1]

Synthesis of Compound 19 was completed by using steps similar to those described in Example 1. Exact Mass (calculated): 473.20; MS(ESI) m/z(M+1)$^+$: 474.2016.

Example 20

Synthesis of Compound 20 (R)-1-(3-(4-amino-3-(4-((methylpiperazin-1-yl)methyl)phenyl)-1H-pyrazolo[3,4-d]pyrimidin-1-yl)piperidin-1-yl)prop-2-en-1-one

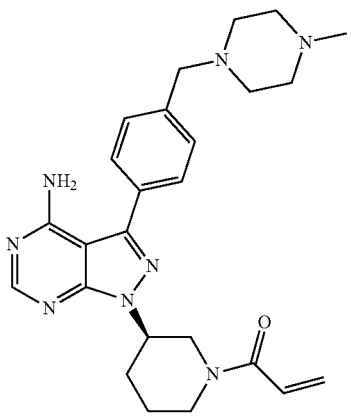 [SMILES: C=CC(=O)N1CCC[C@@H](n2nc(-c3ccc(CN4CCN(C)CC4)cc3)c3c(N)ncnc32)C1]

Synthesis of Compound 20 was completed by using steps similar to those described in Example 1. Exact Mass (calculated): 460.27; MS(ESI) m/z(M+1)$^+$: 461.2713.

Example 21

Synthesis of Compound 21 (R)-1-(3-(4-amino-3-(3-chloro-4-((4-fluorobenzyl)oxy)phenyl)-1H-pyrazolo[3,4-d]pyrimidin-1-yl)piperidin-1-yl)prop-2-en-1-one

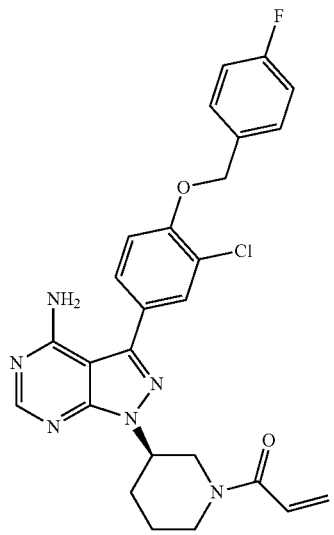 [SMILES: C=CC(=O)N1CCC[C@@H](n2nc(-c3ccc(OCc4ccc(F)cc4)c(Cl)c3)c3c(N)ncnc32)C1]

Synthesis of Compound 21 was completed by using steps similar to those described in Example 1. Exact Mass (calculated): 506.16; MS(ESI) m/z(M+1)$^+$: 507.1711.

Example 22

Synthesis of Compound 22 (R)-1-(3-(4-amino-3-(3-chloro-4-((3,4-difluorobenzyl)oxy)phenyl)-1H-pyrazolo[3,4-d]pyrimidin-1-yl)piperidin-1-yl)prop-2-en-1-one

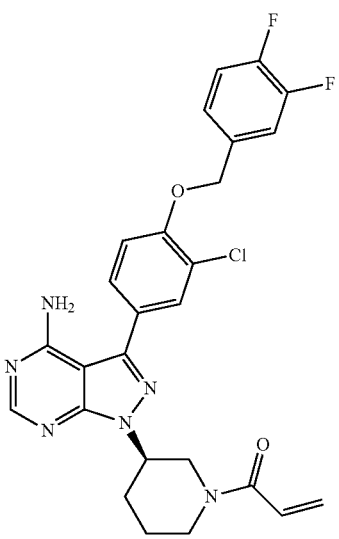 [SMILES: C=CC(=O)N1CCC[C@@H](n2nc(-c3ccc(OCc4ccc(F)c(F)c4)c(Cl)c3)c3c(N)ncnc32)C1]

Synthesis of Compound 22 was completed by using steps similar to those described in Example 1. Exact Mass (calculated): 524.15; MS(ESI) m/z(M+1)$^+$: 525.1608.

Example 23

Synthesis of Compound 23 (R)-1-(3-(4-amino-3-(3-chloro-4-((2,5-difluorobenzyl)oxy)phenyl)-1H-pyrazolo[3,4-d]pyrimidin-1-yl)piperidin-1-yl)prop-2-en-1-one

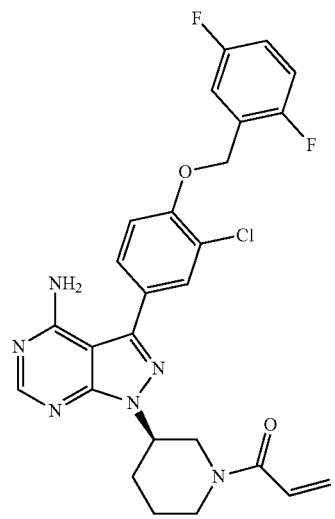 [SMILES: C=CC(=O)N1CCC[C@@H](n2nc(-c3ccc(OCc4cc(F)ccc4F)c(Cl)c3)c3c(N)ncnc32)C1]

Synthesis of Compound 23 was completed by using steps similar to those described in Example 1. Exact Mass (calculated): 524.15; MS(ESI) m/z(M+1)$^+$: 525.1607.

Example 24

Synthesis of Compound 24 (R)-1-(3-(4-amino-3-(2-fluoro-4-((3-fluorobenzyl)oxy)phenyl)-1H-pyrazolo[3,4-d]pyrimidin-1-yl)piperidin-1-yl)prop-2-en-1-one

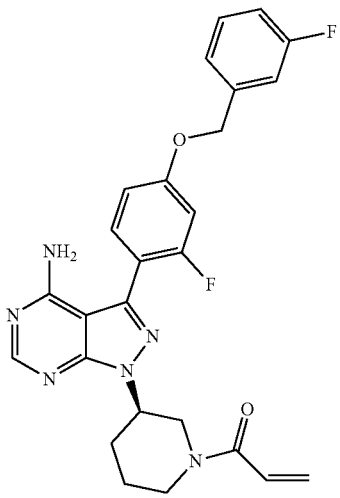

Synthesis of Compound 24 was completed by using steps similar to those described in Example 1. Exact Mass (calculated): 490.19; MS(ESI) m/z(M+1)$^+$: 491.2013.

Example 25

Synthesis of Compound 25 (R)-1-(3-(4-amino-3-(3,6-dichloro-4-((3-fluorobenzyl)oxy)phenyl)-1H-pyrazolo[3,4-d]pyrimidin-1-yl)piperidin-1-yl)prop-2-en-1-one

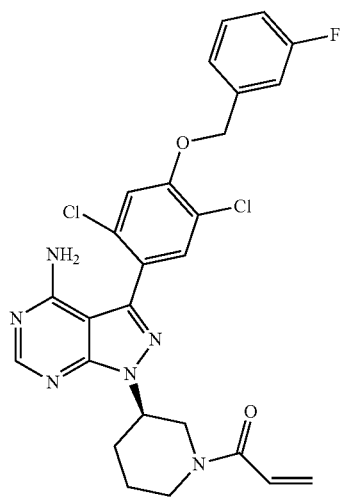 [SMILES: C=CC(=O)N1CCC[C@@H](n2nc(-c3cc(Cl)c(OCc4cccc(F)c4)cc3Cl)c3c(N)ncnc32)C1]

Synthesis of Compound 25 was completed by using steps similar to those described in Example 1. Exact Mass (calculated): 540.12; MS(ESI) m/z(M+1)$^+$: 541.1315.

Example 26

Synthesis of Compound 26 (R)-1-(3-(4-amino-3-(2-chloro-4-((3-fluorobenzyl)oxy)phenyl)-1H-pyrazolo[3,4-d]pyrimidin-1-yl)piperidin-1-yl)prop-2-en-1-one

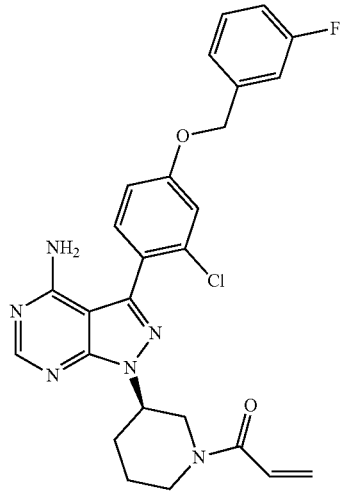 [SMILES: C=CC(=O)N1CCC[C@@H](n2nc(-c3ccc(OCc4cccc(F)c4)cc3Cl)c3c(N)ncnc32)C1]

Synthesis of Compound 26 was completed by using steps similar to those described in Example 1. Exact Mass (calculated): 506.16; MS(ESI) m/z(M+1)$^+$: 507.1720.

Example 27

Synthesis of Compound 27 (R)-1-(3-(4-amino-3-(2-methyl-4-((3-fluorobenzyl)oxy)phenyl)-1H-pyrazolo[3,4-d]pyrimidin-1-yl)piperidin-1-yl)prop-2-en-1-one

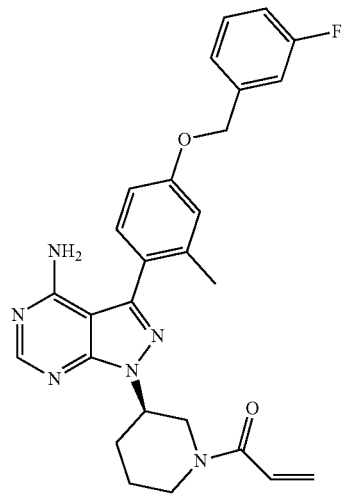 [SMILES: C=CC(=O)N1CCC[C@@H](n2nc(-c3ccc(OCc4cccc(F)c4)cc3C)c3c(N)ncnc32)C1]

Synthesis of Compound 27 was completed by using steps similar to those described in Example 1. Exact Mass (calculated): 486.22; MS(ESI) m/z(M+1)⁺: 487.2224.

Example 28

Synthesis of Compound 28 (R)-1-(3-(4-amino-3-(3-chloro-4-(thiazol-2-ylmethoxy)phenyl)-1H-pyrazolo[3,4-d]pyrimidin-1-yl)piperidin-1-yl)prop-2-en-1-one

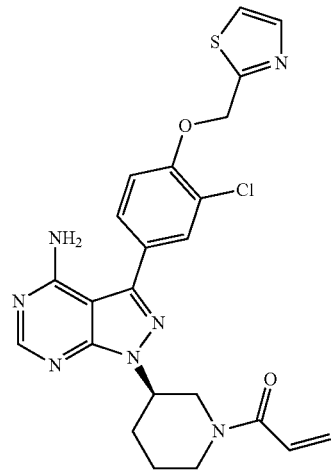 [SMILES: C=CC(=O)N1CCC[C@@H](n2nc(-c3ccc(OCc4nccs4)c(Cl)c3)c3c(N)ncnc32)C1]

Synthesis of Compound 28 was completed by using steps similar to those described in Example 1. Exact Mass (calculated): 495.12; MS(ESI) m/z(M+1)⁺: 496.1313.

Example 29

Synthesis of Compound 29 (R)-1-(3-(4-amino-3-(3-chloro-4-((6-methylpyridin-2-yl)methoxy)phenyl)-1H-pyrazolo[3,4-d]pyrimidin-1-yl)piperidin-1-yl)prop-2-en-1-one

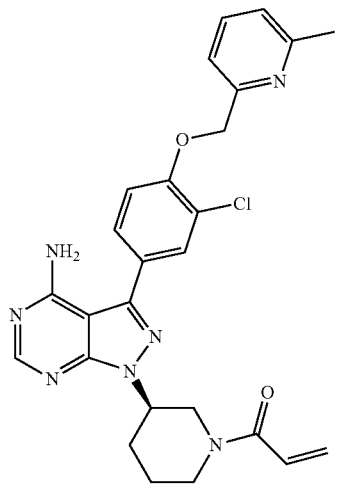 [SMILES: C=CC(=O)N1CCC[C@@H](n2nc(-c3ccc(OCc4cccc(C)n4)c(Cl)c3)c3c(N)ncnc32)C1]

Synthesis of Compound 29 was completed by using steps similar to those described in Example 1. Exact Mass (calculated): 503.18; MS(ESI) m/z(M+1)⁺: 504.1911.

Example 30

Synthesis of Compound 30 (R)-1-(3-(4-amino-3-(3-chloro-4-((6-methylpyridin-3-yl)methoxy)phenyl)-1H-pyrazolo[3,4-d]pyrimidin-1-yl)piperidin-1-yl)prop-2-en-1-one

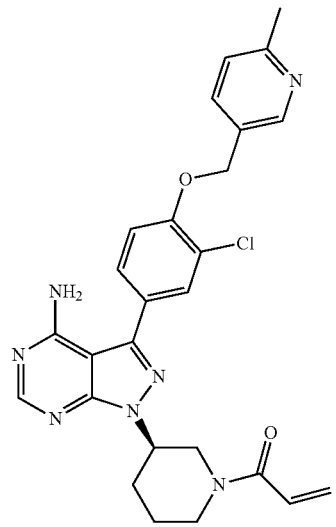 [SMILES: C=CC(=O)N1CCC[C@@H](n2nc(-c3ccc(OCc4ccc(C)nc4)c(Cl)c3)c3c(N)ncnc32)C1]

Synthesis of Compound 30 was completed by using steps similar to those described in Example 1. Exact Mass (calculated): 503.18; MS(ESI) m/z(M+1)⁺: 504.1915.

Example 31

Synthesis of Compound 31 (R)-1-(3-(4-amino-3-(3-chloro-4-flurophenyl)-1H-pyrazolo[3,4-d]pyrimidin-1-yl)piperidin-1-yl)prop-2-en-1-one

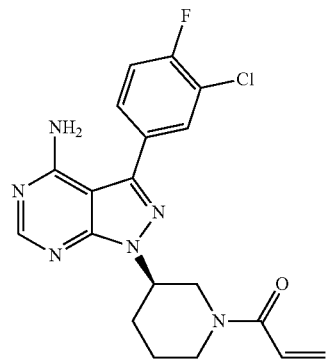 [SMILES: C=CC(=O)N1CCC[C@@H](n2nc(-c3ccc(F)c(Cl)c3)c3c(N)ncnc32)C1]

Synthesis of Compound 31 was completed by using steps similar to those described in Example 1. Exact Mass (calculated): 400.12; MS(ESI) m/z(M+1)⁺: 401.1217.

Example 32

Synthesis of Compound 32 (R)-1-(3-(4-amino-3-(3-chloro-4-flurophenyl)-1H-pyrazolo[3,4-d]pyrimidin-1-yl)piperidin-1-yl)-4-(dimethylamino)but-2-en-1-one

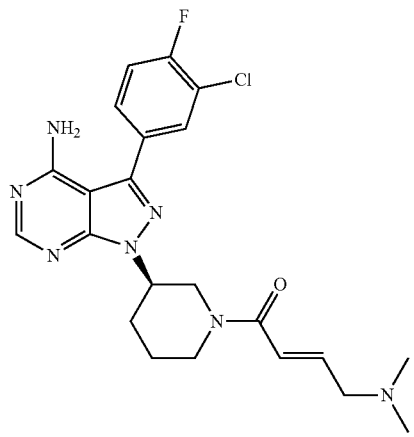 [SMILES: CN(C)C/C=C/C(=O)N1CCC[C@@H](n2nc(-c3ccc(F)c(Cl)c3)c3c(N)ncnc32)C1]

Synthesis of Compound 32 was completed by using steps similar to those described in Example 1. Exact Mass (calculated): 457.18; MS(ESI) m/z(M+1)⁺: 458.1820.

Example 33

Synthesis of Compound 33 (R)-1-(3-(4-amino-3-(3-chloro-4-(furan-2-ylmethoxy)phenyl)-1H-pyrazolo[3,4-d]pyrimidin-1-yl)piperidin-1-yl)prop-2-en-1-one

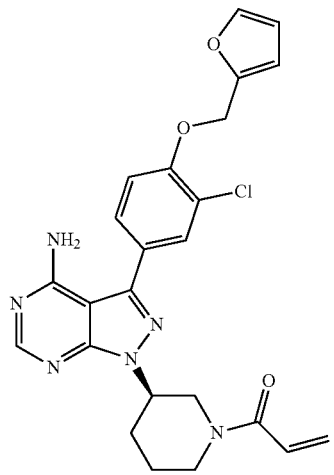 [SMILES: C=CC(=O)N1CCC[C@@H](n2nc(-c3ccc(OCc4ccco4)c(Cl)c3)c3c(N)ncnc32)C1]

Synthesis of Compound 33 was completed by using steps similar to those described in Example 1. Exact Mass (calculated): 478.15; MS(ESI) m/z(M+1)⁺: 479.1621.

Example 34

Synthesis of Compound 34 1-(3-(4-amino-3-(3-chloro-4-((3-fluorobenzyl)oxy)phenyl)-1H-pyrazolo[3,4-d]pyrimidin-1-yl)phenyl) acrylamide

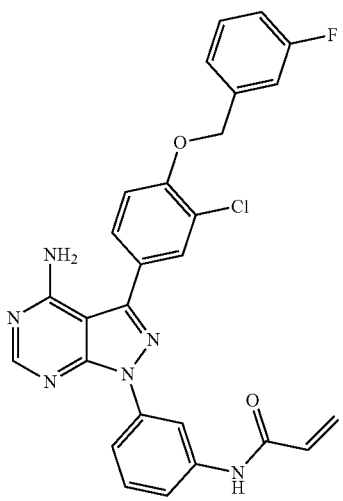 [SMILES: C=CC(=O)Nc1cccc(-n2nc(-c3ccc(OCc4cccc(F)c4)c(Cl)c3)c3c(N)ncnc32)c1]

Synthesis of Compound 34 was completed by using steps similar to those described in Example 1. Exact Mass (calculated): 514.13; MS(ESI) m/z(M+1)⁺: 515.1418.

Example 35

Synthesis of Compound 35 (R)-1-(3-(4-amino-3-(3-trifluoromethyl-4-(pyridin-2-ylmethoxy)phenyl)-1H-pyrazolo[3,4-d]pyrimidin-1-yl)piperidin-1-yl)prop-2-en-1-one

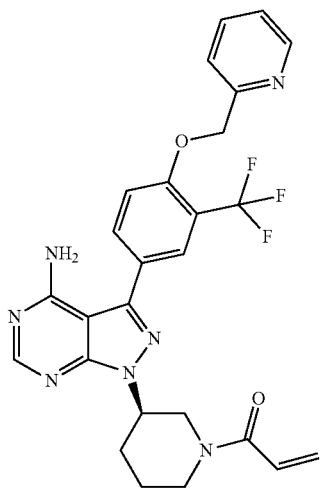 [SMILES: C=CC(=O)N1CCC[C@@H](n2nc(-c3ccc(OCc4ccccn4)c(C(F)(F)F)c3)c3c(N)ncnc32)C1]

Synthesis of Compound 35 was completed by using steps similar to those described in Example 1. Exact Mass (calculated): 523.19; MS(ESI) m/z(M+1)⁺: 524.2012.

Example 36

Synthesis of Compound 36 (R)-1-(3-(4-amino-3-(3-chloro-4-((4-methoxy-3,5-di methyl pyridin-2-yl)methoxy)phenyl)-1H-pyrazolo[3,4-d]pyrimidin-1-yl)piperidin-1-yl)prop-2-en-1-one

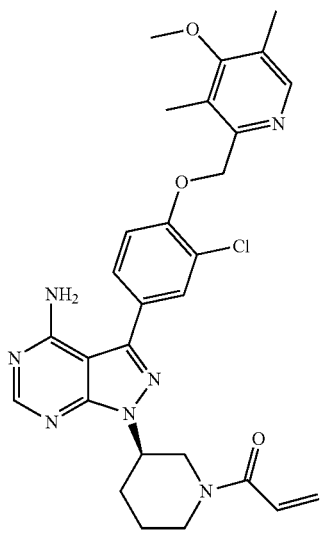

Synthesis of Compound 36 was completed by using steps similar to those described in Example 1. Exact Mass (calculated): 547.21; MS(ESI) m/z(M+1)⁺: 548.2125.

Example 37

Synthesis of Compound 37 (R)-1-(3-(4-amino-3-(3-chloro-4-((1-methyl-1H-imidazol-2-yl)methoxy)phenyl)-1H-pyrazolo[3,4-d]pyrimidin-1-yl)piperidin-1-yl)prop-2-en-1-one

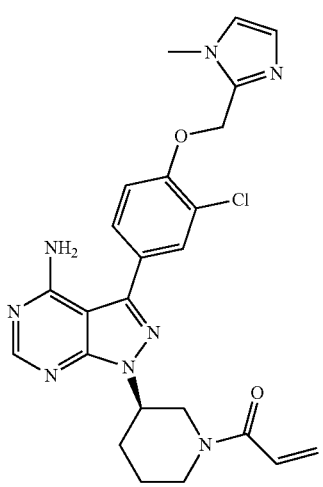 [SMILES: C=CC(=O)N1CCC[C@@H](n2nc(-c3ccc(OCc4nccn4C)c(Cl)c3)c3c(N)ncnc32)C1]

Synthesis of Compound 37 was completed by using steps similar to those described in Example 1. Exact Mass (calculated): 492.18; MS(ESI) m/z(M+1)⁺: 493.1835.

Example 38

Synthesis of Compound 38 N-(5-((4-amino-3-(3-chloro-4-flurophenyl)-1H-pyrazolo[3,4-d]pyrimidin-1-yl)meth yl)-2-flurophenyl)acryloyl chloride

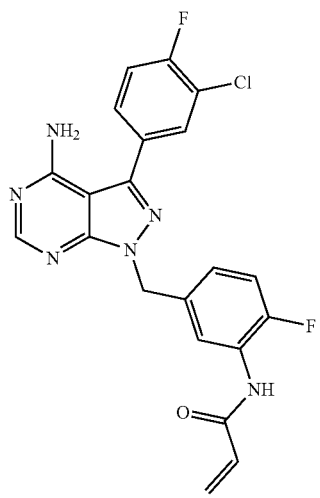 [SMILES: C=CC(=O)Nc1cc(Cn2nc(-c3ccc(F)c(Cl)c3)c3c(N)ncnc32)ccc1F]

Synthesis of Compound 38 was completed by using steps similar to those described in Example 1. Exact Mass (calculated): 440.10; MS(ESI) m/z(M+1)⁺: 441.1056.

Example 39

Synthesis of Compound 39 (R)-1-(3-(4-amino-3-(3-chloro-4-((1-methyl-1H-indazol-3-yl)methoxy)phenyl)-1H-pyrazolo[3,4-d]pyrimidin-1-yl)piperidin-1-yl)prop-2-en-1-one

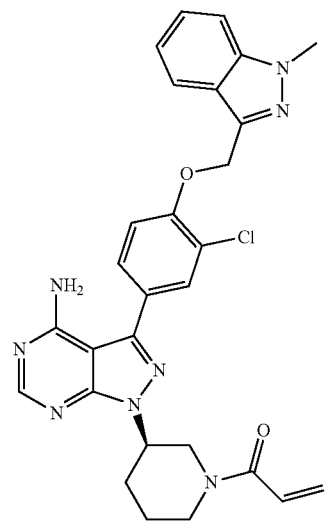 [SMILES: C=CC(=O)N1CCC[C@@H](n2nc(-c3ccc(OCc4nn(C)c5ccccc45)c(Cl)c3)c3c(N)ncnc32)C1]

Synthesis of Compound 39 was completed by using steps similar to those described in Example 1. Exact Mass (calculated): 542.19; MS(ESI) m/z(M+1)$^+$: 543.2023.

Example 40

Synthesis of Compound 40 N-(5-((4-amino-3-(3-chloro-4-fluorophenyl)-1H-pyrazolo[3,4-d]pyrimidin-1-yl)methyl)-2-((2-(dimethylamino)ethyl(methyl)amino)phenyl)acryloyl chloride

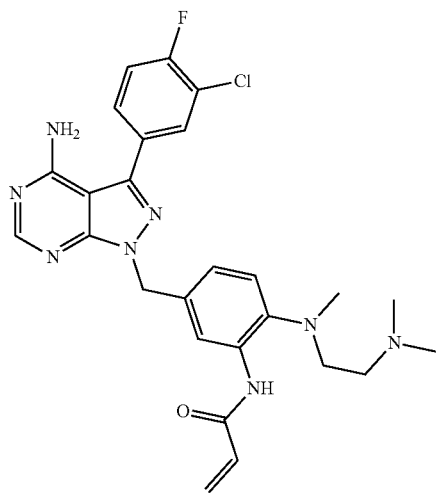 [SMILES: C=CC(=O)Nc1cc(Cn2nc(-c3ccc(F)c(Cl)c3)c3c(N)ncnc32)ccc1N(C)CCN(C)C]

Synthesis of Compound 40 was completed by using steps similar to those described in Example 1. Exact Mass (calculated): 522.21; MS(ESI) m/z(M+1)$^+$: 523.2128.

Example 41

Synthesis of Compound 41 (R)-1-(3-(4-amino-3-(3-chloro-4-((1-methyl-1H-indol-3-yl)methoxy)phenyl)-1H-pyrazolo[3,4-d]pyrimidin-1-yl)piperidin-1-yl)prop-2-en-1-one

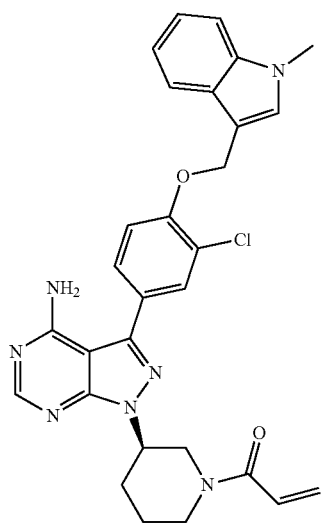 [SMILES: C=CC(=O)N1CCC[C@@H](n2nc(-c3ccc(OCc4cn(C)c5ccccc45)c(Cl)c3)c3c(N)ncnc32)C1]

Synthesis of Compound 41 was completed by using steps similar to those described in Example 1. Exact Mass (calculated): 541.20; MS(ESI) m/z(M+1)$^+$: 542.2031.

Example 42

Synthesis of Compound 42 (R)-1-(3-(4-amino-3-(3-chloro-4-(thien-2-yl)methoxy)phenyl)-1H-pyrazolo[3,4-d]pyrimidin-1-yl)piperidin-1-yl)prop-2-en-1-one

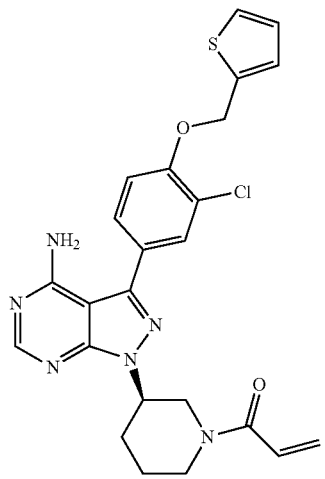 [SMILES: C=CC(=O)N1CCC[C@@H](n2nc(-c3ccc(OCc4cccs4)c(Cl)c3)c3c(N)ncnc32)C1]

Synthesis of Compound 42 was completed by using steps similar to those described in Example 1. Exact Mass (calculated): 494.13; MS(ESI) m/z(M+1)$^+$: 495.1384.

Example 43

Synthesis of Compound 43 (R)-1-(3-(4-amino-3-(3-chloro-4-((5-methylisoxazol-3-yl)methoxy)phenyl)-1H-pyrazolo[3,4-d]pyrimidin-1-yl)piperidin-1-yl)prop-2-en-1-one

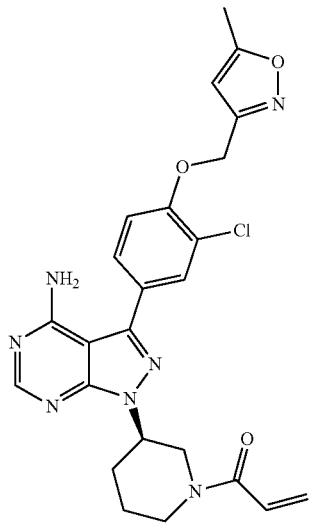 [SMILES: C=CC(=O)N1CCC[C@@H](n2nc(-c3ccc(OCc4cc(C)on4)c(Cl)c3)c3c(N)ncnc32)C1]

Synthesis of Compound 43 was completed by using steps similar to those described in Example 1. Exact Mass (calculated): 493.16; MS(ESI) m/z(M+1)$^+$: 494.1711.

Example 44

Synthesis of Compound 44 (R)-1-(3-(4-amino-3-(3-methyl-4-((4-methoxy-3,5-dimethylpyridin-2-yl)methoxy) phenyl)-1H-pyrazolo[3,4-d]pyrimidin-1-yl)piperidin-1-yl)prop-2-en-1-one

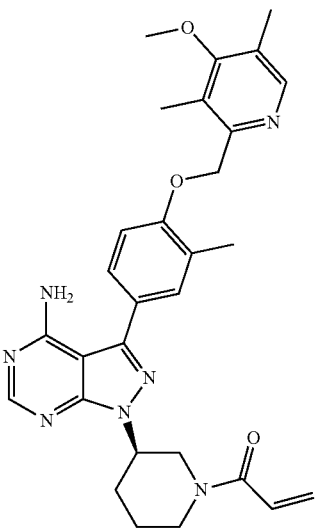 [SMILES: C=CC(=O)N1CCC[C@@H](n2nc(-c3ccc(OCc4ncc(C)c(OC)c4C)c(C)c3)c3c(N)ncnc32)C1]

Synthesis of Compound 44 was completed by using steps similar to those described in Example 1. Exact Mass (calculated): 527.26; MS(ESI) m/z(M+1)$^+$: 528.2719.

Example 45

Synthesis of Compound 45 (R)-1-(3-(4-amino-3-(3-chloro-4-((3-(methanesulfonyl)benzyl)oxy)phenyl)-1H-pyrazolo[3,4-d]pyrimidin-1-yl)piperidin-1-yl)prop-2-en-1-one

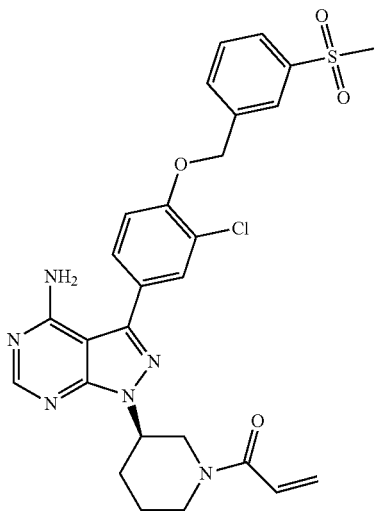 [SMILES: C=CC(=O)N1CCC[C@@H](n2nc(-c3ccc(OCc4cccc(S(C)(=O)=O)c4)c(Cl)c3)c3c(N)ncnc32)C1]

Synthesis of Compound 45 was completed by using steps similar to those described in Example 1. Exact Mass (calculated): 566.15; MS(ESI) m/z(M+1)$^+$: 567.1523.

Example 46

Synthesis of Compound 46 (R)-1-(3-(4-amino-3-(3-chloro-3-(morpholin-4-ylcarbonyl)phenyl)-1H-pyrazolo[3,4-d]pyrimidin-1-yl)piperidin-1-yl)prop-2-en-1-one

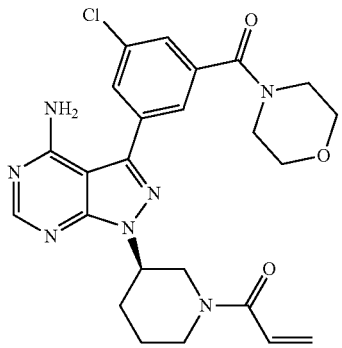 [SMILES: C=CC(=O)N1CCC[C@@H](n2nc(-c3cc(Cl)cc(C(=O)N4CCOCC4)c3)c3c(N)ncnc32)C1]

Synthesis of Compound 46 was completed by using steps similar to those described in Example 1 and following Example 48. Exact Mass (calculated): 495.18; MS(ESI) m/z(M+1)$^+$: 496.1840.

Example 47

Synthesis of Compound 47 (R)-1-(3-(3-(4-((1H-imidazol-2-yl)methoxy)-3-chlorophenyl)-4-amino-1H-pyrazolo[3,4-d]pyrimidin-1-yl)piperidin-1-yl)prop-2-en-1-one

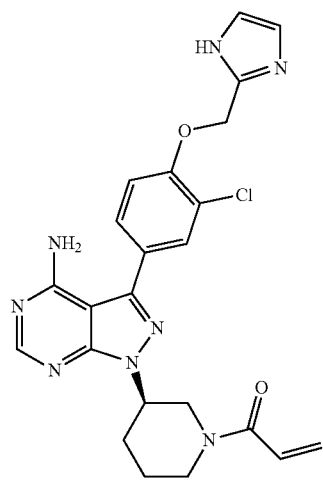 [SMILES: C=CC(=O)N1CCC[C@@H](n2nc(-c3ccc(OCc4ncc[nH]4)c(Cl)c3)c3c(N)ncnc32)C1]

Synthesis of Compound 47 was completed by using steps similar to those described in Example 1. Exact Mass (calculated): 478.16; MS(ESI) m/z(M+1)$^+$: 479.1724.

Example 48

Synthesis of Compound 48 (R)-1-(3-(4-amino-3-(3-chloro-4-(morpholin-4-ylcarbonyl)phenyl)-1H-pyrazolo[3,4-d]pyrimidin-1-yl)piperidin-1-yl)prop-2-en-1-one

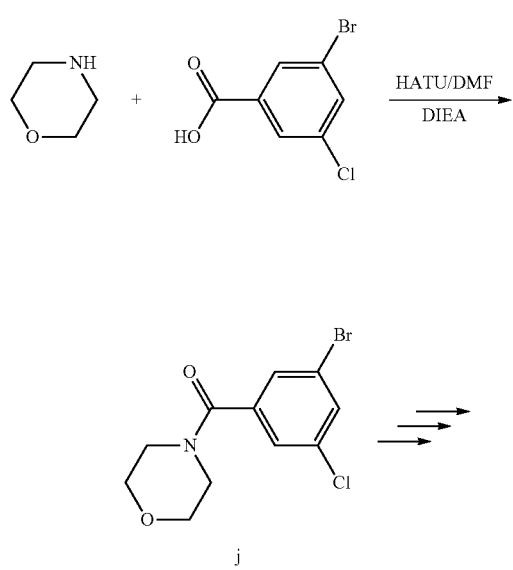

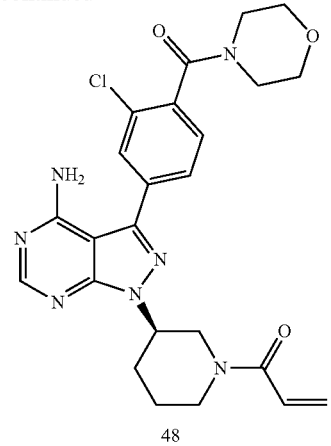

Synthesis of compound j:

3-chloro-5-bromobenzoic acid (2 g, 1 eq), morpholine (0.73 g, 1 eq), 2-(7-azobenzotriazol)-N,N,N',N'-tetramethyluronium hexafluorophosphate (HATU) (3.8 g, 1.2 eq), N,N-diisopropylethylamine (DIEA) (1.4 g, 1.3 eq) and N,N-dimethylformamide DMF (5 mL) were mixed and stirred for 1 h at room temperature, and then diluted with ethyl acetate (100 mL), washed with water (20 mL×3) and saturated NaCl solution, and subjected to concentration to obtain 3 g of solid.

The subsequent steps for synthesizing Compound 48 were completed by using steps similar to those described in Example 1. Exact Mass (calculated): 495.18; MS(ESI) m/z (M+1)$^+$: 496.1836.

Example 49

Synthesis of Compound 49 (R)-4-(1-(1-acryloylpiperidin-3-yl)-4-amino-1H-pyrazolo[3,4-d]pyrimidin-3-yl)-2-chloro-N-morpholinylbenzamide

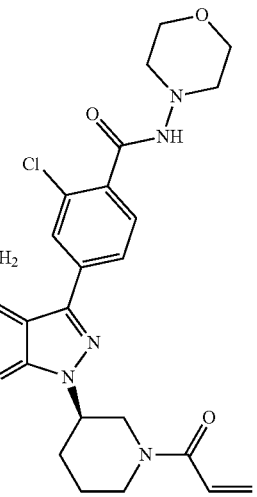

Synthesis of Compound 49 was completed by using steps similar to those described in Example 48 and Example 1. Exact Mass (calculated): 510.19; MS(ESI) m/z(M+1)$^+$: 511.1942.

Example 50

Synthesis of Compound 50 (R)-4-(1-(1-acryloylpip-eridin-3-yl)-4-amino-1H-pyrazolo[3,4-d]pyrimidin-3-yl)-2-chloro-N-(2-morpholinylethyl)benzamide

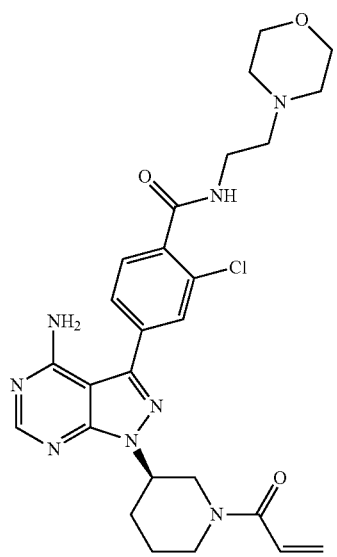 [SMILES: C=CC(=O)N1CCC[C@@H](n2nc(-c3ccc(C(=O)NCCN4CCOCC4)c(Cl)c3)c3c(N)ncnc32)C1]

Synthesis of Compound 50 was completed by using steps similar to those described in Example 48 and Example 1. Exact Mass (calculated): 538.22; MS(ESI) m/z(M+1)⁺: 5539.2248.

Example 51

Synthesis of Compound 51 (R)-1-(3-(4-amino-3-(3-chloro-4-((3-fluorobenzyl)oxy)phenyl)-1H-pyrazolo[3,4-d]pyrimidin-1-yl)piperidin-1-yl)propan-1-one

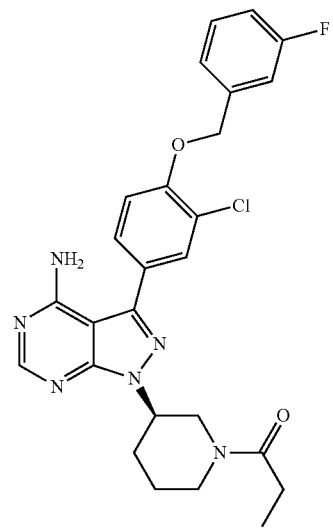 [SMILES: CCC(=O)N1CCC[C@@H](n2nc(-c3ccc(OCc4cccc(F)c4)c(Cl)c3)c3c(N)ncnc32)C1]

Synthesis of Compound 51 was completed by using steps similar to those described in Example 1. Exact Mass (calculated): 508.18; MS(ESI) m/z(M+1)⁺: 509.1834.

Example 52

Synthesis of Compound 52 (R)-1-(3-(4-amino-3-(3-chloro-4-(pyridin-2-ylmethoxy)phenyl)-1H-pyrazolo[3,4-d]pyrimidin-1-yl)piperidin-1-yl)propan-1-one

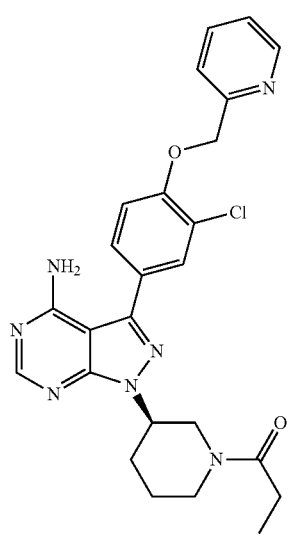

Synthesis of Compound 52 was completed by using steps similar to those described in Example 1. Exact Mass (calculated): 491.18; MS(ESI) m/z(M+1)⁺: 492.1916.

Example 53

Synthesis of Compound 53 (S)-1-(3-(4-amino-3-(3-chloro-4-((3-fluorobenzyl)oxy)phenyl)-1H-pyrazolo[3,4-d]pyrimidin-1-yl)piperidin-1-yl)prop-2-en-1-one

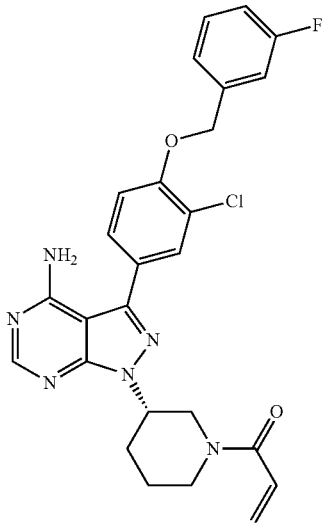 [SMILES: C=CC(=O)N1CCC[C@H](n2nc(-c3ccc(OCc4cccc(F)c4)c(Cl)c3)c3c(N)ncnc32)C1]

Synthesis of Compound 53 was completed by using steps similar to those described in Example 1. Exact Mass (calculated): 506.16; MS(ESI) m/z(M+1)⁺: 507.1711.

Example 54

Synthesis of Compound 54 (S)-1-(3-(4-amino-3-(3-chloro-4-(pyridin-2-ylmethoxy)phenyl)-1H-pyrazolo[3,4-d]pyrimidin-1-yl)piperidin-1-yl)prop-2-en-1-one

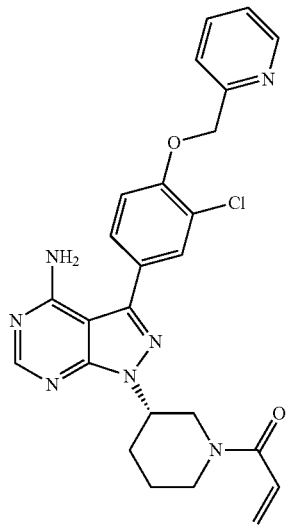 [SMILES: C=CC(=O)N1CCC[C@H](n2nc(-c3ccc(OCc4ccccn4)c(Cl)c3)c3c(N)ncnc32)C1]

Synthesis of Compound 54 was completed by using steps similar to those described in Example 1. Exact Mass (calculated): 489.17; MS(ESI) m/z(M+1)$^+$: 490.1713.

Example 55

Synthesis of Compound 55 (R)-1-(3-(4-amino-3-(6-(pyridin-2-ylmethoxy)pyridin-3-yl)-1H-pyrazolo[3,4-d]pyrimidin-1-yl)piperidin-1-yl)propan-1-one

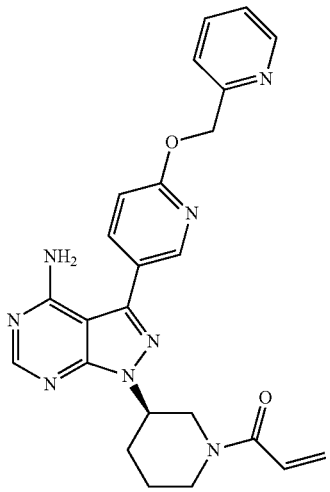 [SMILES: C=CC(=O)N1CCC[C@@H](n2nc(-c3ccc(OCc4ccccn4)nc3)c3c(N)ncnc32)C1]

Synthesis of Compound 55 was completed by using steps similar to those described in Example 1. Exact Mass (calculated): 456.20; MS(ESI) m/z(M+1)$^+$: 457.2122.

Example 56

Synthesis of Compound 56 (R)-1-(3-(4-amino-3-(3-methyl-4-((6-methylpyridin-2-yl)methoxy)phenyl)-1H-pyrazolo[3,4-d]pyrimidin-1-yl)piperidin-1-yl)prop-2-en-1-one

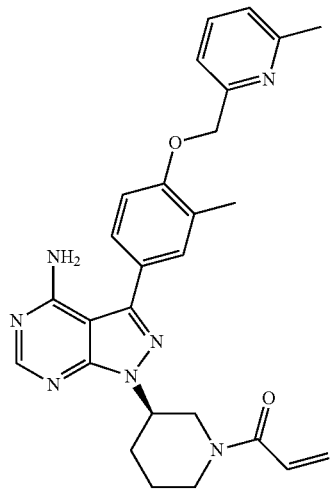 [SMILES: C=CC(=O)N1CCC[C@@H](n2nc(-c3ccc(OCc4cccc(C)n4)c(C)c3)c3c(N)ncnc32)C1]

Synthesis of Compound 56 was completed by using steps similar to those described in Example 1. Exact Mass (calculated): 483.24; MS(ESI) m/z(M+1)$^+$: 484.2436.

Example 57

Synthesis of Compound 57 (R)-1-(3-(4-amino-3-(3-chloro-4-((3,5-dimethyl-1H-pyrazol-1-yl)methoxy)phenyl)-1H-pyrazolo[3,4-d]pyrimidin-1-yl)piperidin-1-yl)prop-2-en-1-one

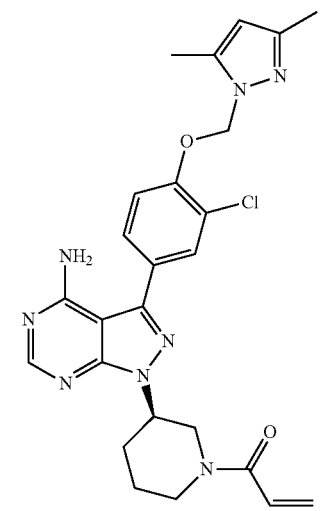 [SMILES: C=CC(=O)N1CCC[C@@H](n2nc(-c3ccc(OCn4nc(C)cc4C)c(Cl)c3)c3c(N)ncnc32)C1]

Synthesis of Compound 57 was completed by using steps similar to those described in Example 1. Exact Mass (calculated): 506.19; MS(ESI) m/z(M+1)$^+$: 507.2016.

Example 58

Synthesis of Compound 58 (R)-1-(3-(4-amino-3-(3-chloro-4-((1,3-dimethyl-1H-pyrazol-5-yl)methoxy)phenyl)-1H-pyrazolo[3,4-d]pyrimidin-1-yl)piperidin-1-yl)prop-2-en-1-one

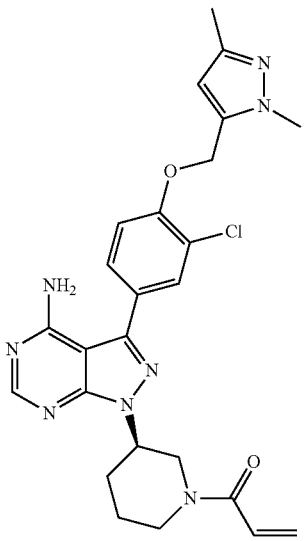 [SMILES: C=CC(=O)N1CCC[C@@H](n2nc(-c3ccc(OCc4cc(C)nn4C)c(Cl)c3)c3c(N)ncnc32)C1]

Synthesis of Compound 58 was completed by using steps similar to those described in Example 1. Exact Mass (calculated): 506.19; MS(ESI) m/z(M+1)$^+$: 507.2021.

Example 59

Synthesis of Compound 59 (R)-1-(3-(4-amino-3-(3-chloro-4-((4-methylthiazol-5-yl)methoxy)phenyl)-1H-pyrazolo[3,4-d]pyrimidin-1-yl)piperidin-1-yl)prop-2-en-1-one

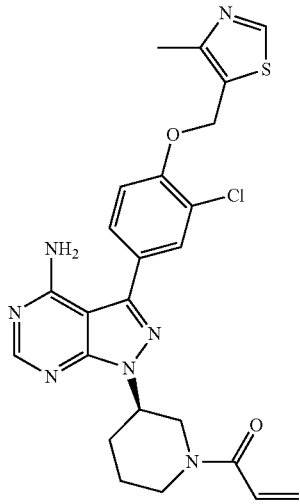 [SMILES: C=CC(=O)N1CCC[C@@H](n2nc(-c3ccc(OCc4scnc4C)c(Cl)c3)c3c(N)ncnc32)C1]

Synthesis of Compound 59 was completed by using steps similar to those described in Example 1. Exact Mass (calculated): 509.14; MS(ESI) m/z(M+1)$^+$: 510.1485.

Example 60

Synthesis of Compound 60 (R)-1-(3-(4-amino-3-(3-chloro-4-((2,4-dimethylthiazol-5-yl)methoxy)phenyl)-1H-pyrazolo[3,4-d]pyrimidin-1-yl)piperidin-1-yl)prop-2-en-1-one

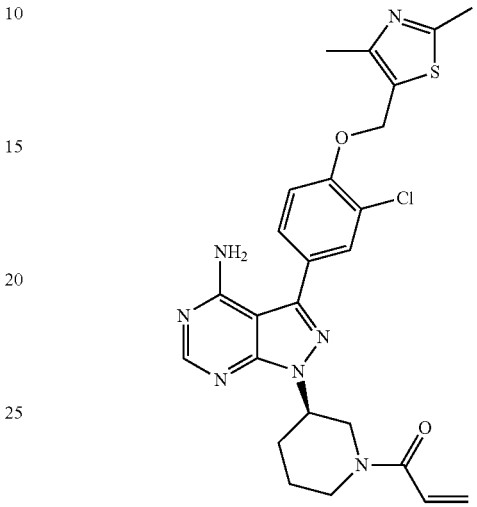

Synthesis of Compound 60 was completed by using steps similar to those described in Example 1. Exact Mass (calculated): 523.16; MS(ESI) m/z(M+1)$^+$: 524.1677.

Example 61

Effects of the Novel Kinase Inhibitor on Growth of Cancer Cells

Compounds of the present invention were further evaluated for their selectivity in inhibiting proliferation of cancer cells by testing effects of the novel kinase inhibitors on proliferation of cancer cells. In the examples the following cells were selected: human non-small cell lung cancer cell NCI-H1975 (expressing EGFR L858R/T790M double-mutant gene), human-derived non-small cell lung cancer cell PC-9 (expressing EGFR delE746_A750 mutant gene), human-derived non-small cell lung cancer cell HCC827 (expressing EGFR delE746_A750 mutant gene), human lung adenocarcinoma cell HCC4006 (expressing EGFR delE746_A750 mutant gene), human non-small cell lung cancer cell NCI-H3255 (expressing EGFR L858R mutant gene), human skin squamous carcinoma cell A431 (expressing wild-type EGFR gene), human non-small cell lung cancer cell A549 (expressing wild-type EGFR gene), human non-small cell lung cancer cell NCI-H460 (expressing wild-type EGFR gene), human non-small cell lung cancer cell NCI-H2122 (expressing wild-type EGFR gene), Chinese hamster ovary (CHO) cell (*Cricetulus griseus*, hamster, Chinese, ovary), Chinese hamster lung cell (CHL), mouse pro-B cell BaF3. The cells above were all purchased from (USA).

In addition, this example further uses: mouse BaF3-TEL-EGFR (stably expressing wild-type EGFR kinase), mouse BaF3-TEL-EGFR-L858R (stably expressing EGFR L858R mutant kinase), mouse BaF3-TEL-EGFR-T790M (stably expressing EGFR T790M mutant kinase), mouse BaF3-FL- EGFR-Del19 (stably expressing EGFR delE746_A750 mutant kinase), mouse BaF3-FL-EGFR-T790M-L858R (stably expressing EGFR T790M/L858R mutant kinase), mouse BaF3/P210 (stably expressing bcr/abl~(P210) mutant kinase), mouse BaF3-TEL-ABL-T315I (stably expressing ABLT315I mutant kinase), mouse BaF3-FLT3-ITD (stably expressing FLT3/ITD mutant kinase), mouse BaF3-TEL-JAK2 (stably expressing JAK2 kinase), mouse BaF3-TEL-JAK3 (stably expressing JAK3 kinase), mouse BaF3-TPR-MET (stably expressing MET kinase), mouse BaF3-TEL-BLK (stably expressing BLK kinase), mouse BaF3-TEL-ABL (stably expressing ABL kinase), mouse BaF3-TEL-BMX (stably expressing BMX kinase), mouse BaF3-TEL-ALK (stably expressing ALK kinase). The above cell lines were all constructed by our laboratory according to the following method: the kinase region sequences of human GFR, EGFR L858R, EGFR T790M, EGFR delE746_A750, EGFR T790M/L858R, bcr/abl~(P210), ABL T315I, FLT3/ITD, JAK2, JAK3, MET, BLK, ABL, BMX, ALK were amplified respectively by PCR, inserted respectively into MSCV-Puro vectors harboring N-terminal fragment and/or NPM fragment and/or TPR fragment (Clontech), then the vectors were stably transfected into mouse BaF3 cells by retrovirus methods and growth factor IL-3 was removed, eventually obtaining cell lines that are transferred protein (EGFR, EGFR L858R, EGFR T790M, EGFR delE746_A750, EGFR T790M/L858R, bcr/abl~(P210), ABL T315I, FLT3/ITD, JAK2, JAK3, MET, BLK, ABL, BMX, ALK)-dependent.

In the example the above cells were respectively added with the compounds of this invention at various concentrations (0.000508 µM, 0.00152 µM, 0.00457 µM, 0.0137 µM, 0.0411 µM, 0.123 µM, 0.370 µM, 1.11 µM, 3.33 µM, 10 µM) as well as control compounds AZD9291 (a third-generation, oral, irreversible mutation-selective EGFR inhibitor, purchased from Haoyuan Chemexpress Co., Ltd.), CO-1686 (a third-generation, oral, irreversible mutation-selective EGFR inhibitor, purchased from Haoyuan Chemexpress Co., Ltd) and BIBW2992 (an irreversible EGFR inhibitor, purchased from Haoyuan Chemexpress Co., Ltd). The cells were incubated for 72 h, and then the number of viable cells was determined via quantitative determination with a microplate reader by using Cell Titer-Glo® (Promega, the USA) Luminescent Cell Viability Assay kit. Test results were shown in Table 1.

TABLE 1

Effects of the novel kinase inhibitors on growth of cancer cells (the results were represented as GI50, µM)

| Cell lines | Compound 1 GI50 (µM) | Compound 2 GI50 (µM) | Compound 3 GI50 (µM) | Compound 4 GI50 (µM) | Compound 6 GI50 (µM) | Compound 7 GI50 (µM) |
|---|---|---|---|---|---|---|
| NCI-H1975 | 0.005 | 0.005 | 0.48 | 0.053 | 6.9 | 0.12 |
| PC-9 | 0.004 | <0.003 | 0.11 | 0.028 | 0.46 | 0.019 |
| HCC827 | 0.015 | <0.003 | 0.61 | 0.038 | 0.81 | 0.063 |
| HCC4006 | | <0.003 | 0.61 | | | |
| NCI-H3255 | 0.022 | 0.015 | 1.1 | 0.028 | 0.41 | 0.055 |
| A431 | 0.002 | 0.004 | 4.1 | 0.017 | | |
| A549 | >10 | 8.4 | 5.5 | 3.7 | 4.3 | 1.6 |
| NCI-H460 | | | | | | |
| NCI-H2122 | >10 | 1.1 | 2.1 | 0.13 | | |
| CHO | >10 | 5.8 | | | | |
| CHL | >10 | 5.7 | | | | |
| BaF3 | >10 | 1.5 | 1.7 | 4.1 | 1.3 | 3.7 |
| BaF3-TEL-EGFR | 2.0 | 3.5 | 3.6 | 0.013 | | |
| BaF3-TEL-EGFR-L858R | <0.003 | <0.003 | 0.097 | <0.0003 | | |
| BaF3-TEL-EGFR-T790M | <0.003 | <0.003 | 0.11 | | 0.47 | |
| BaF3-FL-EGFR-Del19 | 0.004 | <0.003 | 0.063 | | | |
| BaF3-FL-EGFR-T790M-L858R | <0.0003 | <0.0003 | 0.3 | <0.0003 | | 0.042 |
| BaF3-P210 | 2.8 | 2.4 | | | | |
| BaF3-TEL-ABL-T315I | >10 | 4.07 | | | | |
| BaF3-FLT3-ITD | 7.2 | 2.8 | | | | |
| BaF3-TEL-JAK2 | 4.2 | 1.6 | | | | |
| BaF3-TEL-JAK3 | 0.8 | 1.0 | | | | |
| BaF3-TPR-MET | >10 | 5.8 | | | | |
| BaF3-TEL-BLK | 0.042 | 0.047 | | | | |
| BaF3-TEL-ABL | >10 | 4.7 | | | | |
| BaF3-TEL-BMX | <0.0003 | <0.0003 | | | | |
| BaF3-TEL-ALK | >10 | 5.8 | | | | |

| Cell lines | Compound 8 GI50 (µM) | Compound 9 GI50 (µM) | Compound 10 GI50 (µM) | Compound 11 GI50 (µM) | Compound 12 GI50 (µM) |
|---|---|---|---|---|---|
| NCI-H1975 | 0.35 | 0.071 | 0.55 | 1.6 | 0.080 |
| PC-9 | 0.025 | 0.051 | 0.24 | 0.51 | 0.011 |
| HCC827 | 0.084 | 0.11 | 0.24 | 0.44 | 0.039 |
| HCC4006 | | | | | |
| NCI-H3255 | 0.056 | 0.04 | 0.086 | 0.31 | 0.023 |
| A431 | | | | | |
| A549 | 2.7 | >10 | >10 | >10 | 4.3 |
| NCI-H460 | | | | | |
| NCI-H2122 | | | | | |
| CHO | | | | | |
| CHL | | | | | |

TABLE 1-continued

Effects of the novel kinase inhibitors on growth of cancer cells (the results were represented as GI50, μM)

| Cell lines | | | | | |
|---|---|---|---|---|---|
| BaF3 | >10 | >10 | >10 | >10 | 7.4 |
| BaF3-TEL-EGFR | | | | | 2.8 |
| BaF3-TEL-EGFR-L858R | | | | | |
| BaF3-TEL-EGFR-T790M | | 0.15 | 2.7 | 2.2 | <0.0003 |
| BaF3-FL-EGFR-Del19 | | | | | |
| BaF3-FL-EGFR-T790M-L858R | 0.043 | 0.004 | 0.12 | 0.12 | |

| Cell lines | Compound 13 GI50 (μM) | Compound 14 GI50 (μM) | Compound 15 GI50 (μM) | Compound 16 GI50 (μM) | Compound 17 GI50 (μM) | Compound 18 GI50 (μM) |
|---|---|---|---|---|---|---|
| NCI-H1975 | 0.017 | 0.038 | 0.018 | | | |
| PC-9 | 0.002 | 0.016 | 0.011 | 0.051 | 0.098 | 0.014 |
| HCC827 | 0.016 | | | | | |
| HCC4006 | | | | | | |
| NCI-H3255 | 0.015 | 0.009 | 0.005 | 0.028 | 0.04 | 0.02 |
| A431 | | | | | | |
| A549 | 7.0 | | | | | |
| NCI-H460 | | | | | | |
| NCI-H2122 | | | | | | |
| CHO | | | | | | |
| CHL | | | | | | |
| BaF3 | 5.1 | 2.5 | 4.8 | >10 | >10 | 8.5 |
| BaF3-TEL-EGFR | 2.8 | 1.4 | 2.1 | >10 | >10 | 4.2 |
| BaF3-TEL-EGFR-L858R | | | | | | |
| BaF3-TEL-EGFR-T790M | <0.3 nM | | | | | |
| BaF3-FL-EGFR-Del19 | | | | | | |
| BaF3-FL-EGFR-T790M-L858R | | <0.0003 | <0.0003 | 0.052 | 0.042 | 0.001 |

| Cell lines | Compound 19 GI50 (μM) | Compound 20 GI50 (μM) | Compound 21 GI50 (μM) | Compound 22 GI50 (μM) | Compound 23 GI50 (μM) | Compound 24 GI50 (μM) |
|---|---|---|---|---|---|---|
| NCI-H1975 | >10 | >10 | 0.054 | 0.068 | 0.007 | 1.6 |
| PC-9 | >10 | 7.0 | 0.038 | 0.023 | 0.007 | 0.006 |
| HCC827 | | | | | | |
| HCC4006 | | | | | | |
| NCI-H3255 | >10 | 4.9 | 0.033 | 0.016 | <0.0003 | <0.0003 |
| A431 | | | | | | |
| A549 | | >10 | 3.1 | 2.2 | 3.8 | >10 |
| NCI-H460 | | | | | | |
| NCI-H2122 | | | | | | |
| CHO | | | | | | |
| CHL | | | | | | |
| BaF3 | >10 | >10 | 5.6 | 2.9 | 4.3 | 1.9 |
| BaF3-TEL-EGFR | | | | | | |
| BaF3-TEL-EGFR-L858R | | | | | | |
| BaF3-TEL-EGFR-T790M | | | | | | |
| BaF3-FL-EGFR-Del19 | | | | | | |
| BaF3-FL-EGFR-T790M-L858R | | >10 | 0.008 | 0.002 | <0.0003 | <0.0003 |

| Cell lines | Compound 25 GI50 (μM) | Compound 26 GI50 (μM) | Compound 28 GI50 (μM) | Compound 29 GI50 (μM) | Compound 30 GI50 (μM) |
|---|---|---|---|---|---|
| NCI-H1975 | 7.4 | 2.9 | 0.008 | <0.0003 | 0.003 |
| PC-9 | <0.0003 | 0.048 | 0.01 | 0.035 | 0.038 |
| HCC827 | | | | 0.036 | |
| HCC4006 | | | | | |
| NCI-H3255 | <0.0003 | 0.1 | <0.0003 | 0.027 | 0.036 |
| A431 | | | >10 | >10 | >10 |
| A549 | 8.6 | >10 | >10 | >10 | >10 |
| NCI-H460 | | | | 4.0 | |
| NCI-H2122 | | | | | |
| CHO | | | | | |
| CHL | | | | | |
| BaF3 | 5.5 | 2.3 | 9.8 | >10 | >10 |
| BaF3-TEL-EGFR | | | 2.8 | 5.4 | 3.3 |
| BaF3-TEL-EGFR-L858R | | | | <0.0003 | |
| BaF3-TEL-EGFR-T790M | | | | <0.0003 | |
| BaF3-FL-EGFR-Del19 | | | | | |
| BaF3-FL-EGFR-T790M-L858R | <0.0003 | 0.021 | 0.002 | 0.006 | 0.002 |

| Cell lines | Compound 31 GI50 (μM) | Compound 32 GI50 (μM) | Compound 34 GI50 (μM) | Compound 35 GI50 (μM) | Compound 36 GI50 (μM) |
|---|---|---|---|---|---|
| NCI-H1975 | 0.095 | 0.71 | 3 | 0.056 | <0.0003 |
| PC-9 | 0.009 | 0.17 | >10 | 0.18 | 0.024 |
| HCC827 | | | | | |

TABLE 1-continued

Effects of the novel kinase inhibitors on growth of cancer cells (the results were represented as GI50, μM)

| Cell lines | | | | | |
|---|---|---|---|---|---|
| HCC4006 | | | | | |
| NCI-H3255 | 0.043 | 0.33 | 0.73 | 0.046 | 0.044 |
| A431 | >10 | 3.9 | >10 | >10 | >10 |
| A549 | >10 | >10 | >10 | 3.1 | 3.4 |
| NCI-H460 | | | | | |
| NCI-H2122 | | | | | |
| CHO | | | | | |
| CHL | | | | | |
| BaF3 | >10 | 4.5 | | >10 | >10 |
| BaF3-TEL-EGFR | 2.2 | 0.69 | >10 | 3.6 | 3.5 |
| BaF3-TEL-EGFR-L858R | | | | | |
| BaF3-TEL-EGFR-T790M | | | | | |
| BaF3-FL-EGFR-Del19 | | | | | |
| BaF3-FL-EGFR-T790M-L858R | 0.053 | 0.13 | | <0.0003 | <0.0003 |

| Cell lines | Compound 37 GI50 (μM) | Compound 38 GI50 (μM) | Compound 39 GI50 (μM) | Compound 40 GI50 (μM) | Compound 51 GI50 (μM) | Compound 52 GI50 (μM) |
|---|---|---|---|---|---|---|
| NCI-H1975 | >10 | 5.1 | 0.2 | 1.2 | 2.7 | 3.0 |
| PC-9 | 0.005 | 1.7 | 0.14 | 1.0 | 3.2 | >10 |
| HCC827 | 0.018 | | 0.32 | 1.6 | 3.9 | >10 |
| HCC4006 | | | | | | |
| NCI-H3255 | 0.005 | 3.8 | 0.1 | 3.7 | >10 | >10 |
| A431 | >10 | 8.7 | 2.4 | 2.6 | 9.0 | >10 |
| A549 | 6.2 | 2.8 | 1.1 | | >10 | >10 |
| NCI-H460 | >10 | | | | | |
| NCI-H2122 | | | | | 3.9 | >10 |
| CHO | | | | | | |
| CHL | | | | | | |
| BaF3 | >10 | 4.6 | 3.3 | 1.9 | 9.2 | >10 |
| BaF3-TEL-EGFR | >10 | 6.6 | 3.5 | 1.3 | 3.7 | >10 |
| BaF3-TEL-EGFR-L858R | 0.012 | | | | 0.94 | 1.6 |
| BaF3-TEL-EGFR-T790M | 0.037 | | | | 1.1 | 1.1 |
| BaF3-FL-EGFR-Del19 | | | | | 1.2 | 6.3 |
| BaF3-FL-EGFR-T790M-L858R | | | | | 1.7 | 3.2 |

| Cell lines | Compound 53 GI50 (μM) | Compound 54 GI50 (μM) | CO-1686 GI50 (μM) | AZD9291 GI50 (μM) | BIBW2992 GI50 (μM) |
|---|---|---|---|---|---|
| NCI-H1975 | 0.051 | 0.22 | 0.44 | 0.037 | 0.33 |
| PC-9 | 0.1 | 0.14 | 0.13 | 0.003 | 0.003 |
| HCC827 | 0.12 | 0.23 | 0.097 | 0.004 | 0.001 |
| HCC4006 | | | | | |
| NCI-H3255 | 0.12 | 0.13 | 0.25 | 0.031 | 0.001 |
| A431 | | 0.035 | 1.2 | 0.096 | 0.3-1 |
| A549 | 8.3 | 8.9 | 0.83 | 5.0 | 7.5 |
| NCI-H460 | | | 2.5 | 4.0 | 3.8 |
| NCI-H2122 | 0.63 | 0.3 | | | |
| CHO | | | | | |
| CHL | | | | | |
| BaF3 | 9.4 | >10 | 0.97 | 2.7 | 1.3 |
| BaF3-TEL-EGFR | | 0.049 | 2.8 | 1.8 | 1.3 |
| BaF3-TEL-EGFR-L858R | 0.005 | 0.027 | 0.0063 | 0.0017 | <0.0003 |
| BaF3-TEL-EGFR-T790M | 0.07 | | 0.13 | 0.022 | 0.12 |
| BaF3-FL-EGFR-Del19 | | 0.009 | | | |
| BaF3-FL-EGFR-T790M-L858R | 0.014 | 0.006 | | | |

Example 62

Effect of the Novel Kinase Inhibitors on Cell Signaling Pathways

By assaying a number of cellular biochemical and functional endpoints, Compound 1, Compound 29 and Compound 37 were evaluated for their effects on EGFR as well as other protein kinases (such as Stat3, AKT, ErK, eIF4E, 4EBP1, P70S6K, etc) involved in signaling in the following types of cells: human non-small cell lung cancer cells A549 (expressing wild-type EGFR gene), human non-small cell lung cancer cells H1975 (expressing EGFR L858R/T790M double-mutant gene), human non-small cell lung cancer cells PC-9 (expressing EGFR delE746_A750 mutant gene), human non-small cell lung cancer cells H3255 (expressing EGFR L858R mutant gene), and human non-small cell lung cancer cells HCC827 (expressing EGFR delE746_A750 mutant gene) (all purchased from ATCC, USA). After 4 hour-treatment of the above five types of cells respectively with different concentrations (0 μM, 0.01 μM, 0.03 μM, 0.1 μM, 0.3 μM, 1 μM, 3 μM) of Compound 1, Compound 29, Compound 37 and 1 μM of control Compound AZD9291 (a third-generation, oral, irreversible mutation-selective EGFR inhibitor), 1 μM of control compound Gefitinib (EGFR inhibitor), 1 μM of control compound CO-1686 (a third-generation, oral, irreversible mutation-selective EGFR inhibitor), samples were collected. Effects of Compound 1, Compound 29 and Compound 37 on phosphorylation of Stat3Y705, AKT T308, AKT S473, Erk T202/204, EGFR Y1068, P70S6K Thr389, eIF4E Ser209, 4EBP1 (Thr37/46) in such cells were determined (FIG. 1).

The experimental results showed that: in human non-small cell lung cancer cells A549 (expressing wild-type EGFR gene), human non-small cell lung cancer cells H1975 (expressing EGFRL858R/T790M double-mutant gene), human non-small cell lung cancer cells PC-9 (expressing EGFR19 delE746_A750 mutant gene), human non-small cell lung cancer cells H3255 (expressing EGFR L858R mutant gene), and human non-small cell lung cancer cells HCC827 (expressing EGFR delE746_A750 mutant gene), Compound 1, Compound 29 and Compound 37 could all strongly inhibit phosphorylation of EGFR protein, and meanwhile had a significant effect on phosphorylation of proteins such as AKT308, eIF4E, P70S6K and ERK downstream of EGFR. In the same experiment, similar performance was observed for control compounds AZD9291, CO-1686, Gefitinib at 1 µM.

Example 63

Effect of the Novel Kinase Inhibitors on Cell Apoptosis

To study whether cell death after compound treatment is caused by cell apoptosis or necrosis, effects of Compound 1 on protein cleavage of the DNA repairase poly(ADP-ribose) polymerase (PARP) and Caspase (cysteinyl aspartate-specific proteinase) 3 that were closely related to cell apoptosis was detected in the following five types of cells: human non-small cell lung cancer cells A549 (expressing wild-type EGFR gene), human non-small cell lung cancer cells H1975 (expressing EGFR L858R/T790M double-mutant gene), human non-small cell lung cancer cells PC-9 (expressing EGFR delE746_A750 mutant gene), human non-small cell lung cancer cells H3255 (expressing EGFR L858R mutant gene), and human non-small cell lung cancer cells HCC827 (expressing EGFR delE746_A750 mutant gene) (all purchased from ATCC). Various types of human non-small cell lung cancer cells were respectively treated with a series of concentrations (0 µM, 0.01 µM, 0.03 µM, 0.1 µM, 0.3 µM, 1 µM, 3 µM) of Compound 1 and 1 µM of AZD9291, CO-1686, and cells were collected after 48 hours or 72 hours. Western Blot was used to detect the effects of different concentrations of compounds on protein cleavage of the DNA repairase poly(ADP-ribose) polymerase (PARP) and Caspase (cysteinyl aspartate-specific proteinase) 3 at different time intervals.

Figure 2:
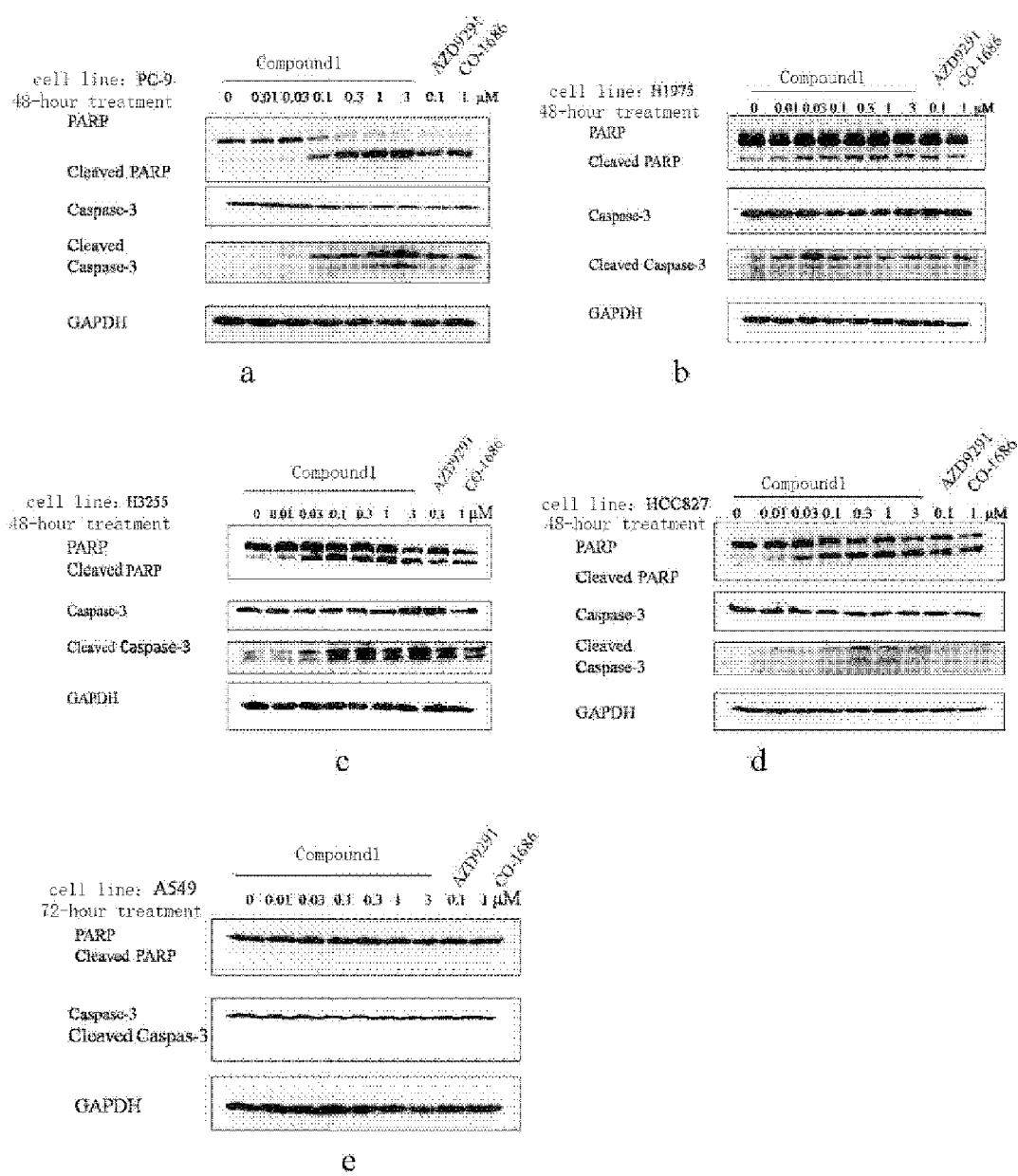
FIG. 2 is a drawing of cell apoptosis which illustrates the effects of Compound 1 on protein cleavage of the DNA repairase poly(ADP-ribose) polymerase (PARP) and Caspase (cysteinyl aspartate-specific proteinase) 3 that are closely related to cell apoptosis in various cells (FIG. 2a: PC-9 cells.
Figure 3A:
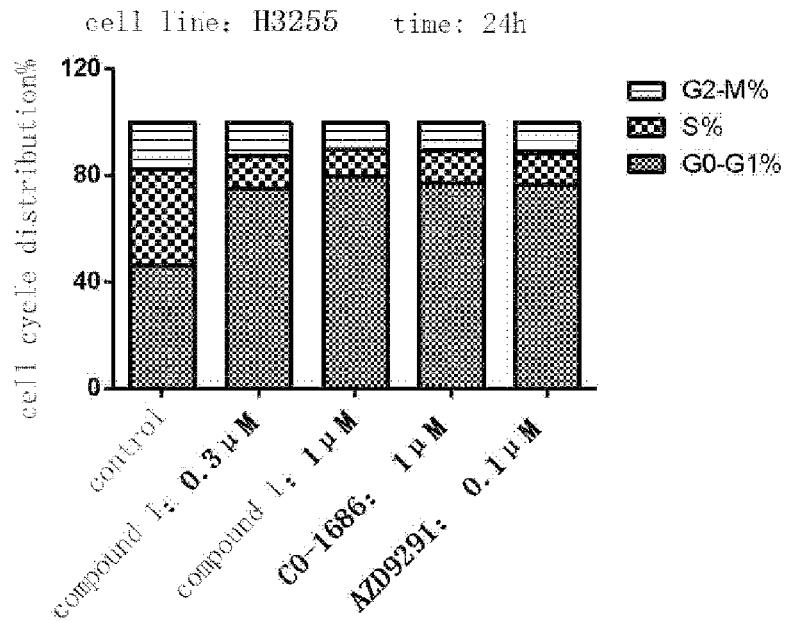
FIG. 3 is a drawing of cell cycle distribution which illustrates the effects of different concentrations of Compound 1 and control Compounds on the cell cycle distribution of various cells (FIG. 3a: H3255 cells.
FIG. 3b: H1975 cells.
FIG. 3c: PC-9 cells.
FIG. 3d: HCC827 cells.
FIG. 3e: A549 cells)
Figure 3B:
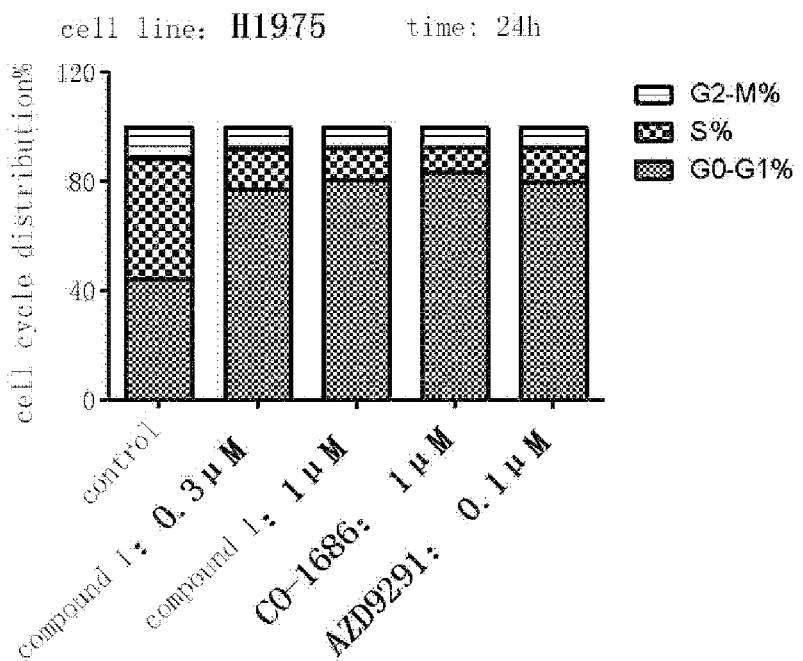
Figure 3C:
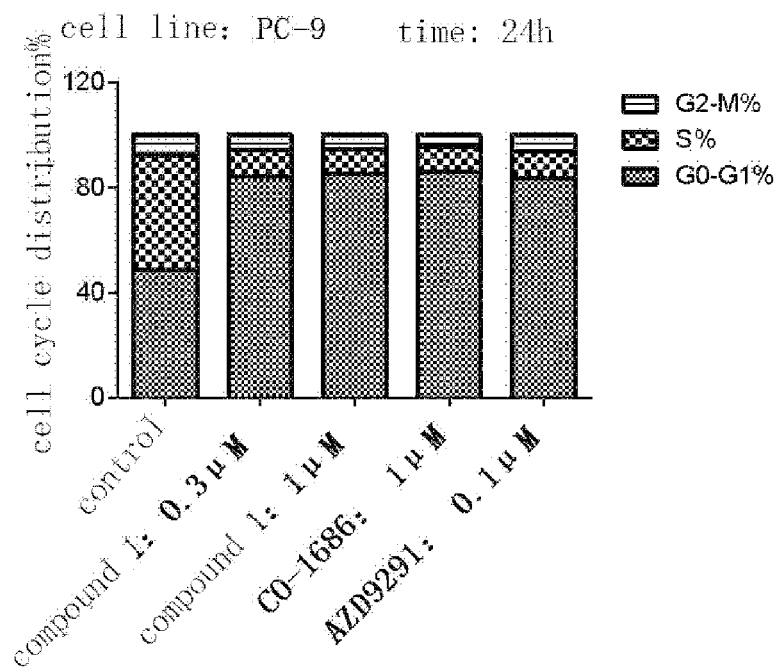
Figure 3D:
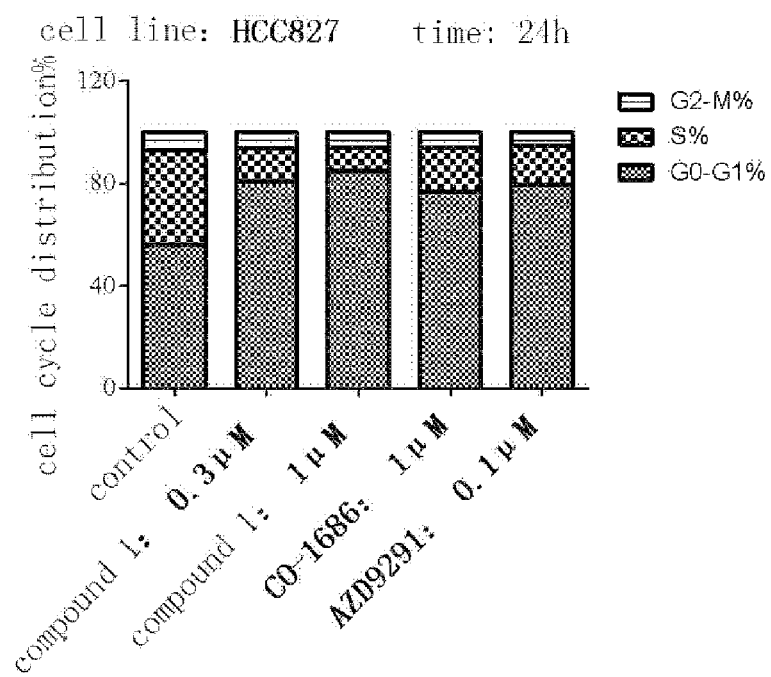
Figure 3E:
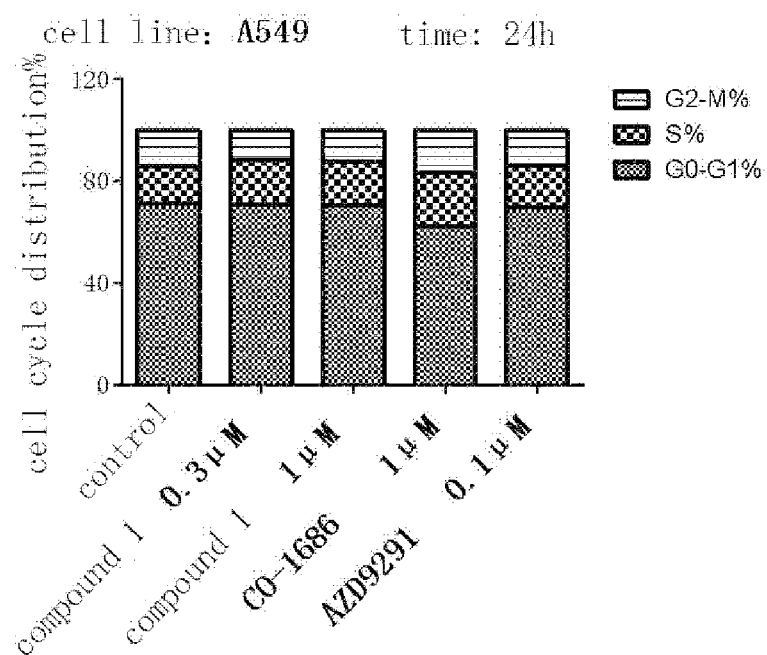

Experimental results were shown in FIG. 2: no cleavage of either the DNA repairase poly(ADP-ribose) polymerase (PARP) or Caspase 3 downstream of PARP was observed in human non-small cell lung cancer cells A549 (expressing wild-type EGFR gene) after 72 hour's treatment. It was proved that Compound 1 failed to induce cell apoptosis in human non-small cell lung cancer cells A549 (expressing wild-type EGFR gene). However, as to human non-small cell lung cancer cells H1975 (expressing EGFR L858R/T790M double-mutant gene), human non-small cell lung cancer cells PC-9 (expressing EGFR delE746_A750 mutant gene), human non-small cell lung cancer cells HCC827 (expressing EGFR delE746_A750 mutant gene) and human non-small cell lung cancer cells H3255 (expressing EGFR L858R mutant gene), significant cleavage of the DNA repairase poly(ADP-ribose) polymerase (PARP) was observed in all cells after 48 hour's administration of the compound at 0.03 µM, and cleavage of the Caspase 3 downstream of PARP was also observed. It was proven that Compound 1 was able to induce cell apoptosis in human non-small cell lung cancer cells H1975 (expressing EGFR L858R/T790M double-mutant gene), human non-small cell lung cancer cells PC-9 (expressing EGFR delE746_A750 mutant gene), human non-small cell lung cancer cells H3255 (expressing EGFR L858R mutant gene), and human non-small cell lung cancer cells HCC827 (expressing EGFR delE746_A750 mutant gene).

Example 64

Effect of the Novel Kinase Inhibitors on Cell Cycle

In human non-small cell lung cancer cells A549 (expressing wild-type EGFR gene), human non-small cell lung cancer cells H1975 (expressing EGFR L858R/T790M double-mutant gene), human non-small cell lung cancer cells PC-9 (expressing EGFR delE746_A750 mutant gene), human non-small cell lung cancer cells H3255 (expressing EGFR L858R mutant gene), and human non-small cell lung cancer cells HCC827 (expressing EGFR delE746_A750 mutant gene), effect of Compound 1 on cell cycle distribution of these cells was examined in order to study the growth cycle to which the cells were blocked upon compound administration. The above cells were treated with a series of concentrations (0 µM, 0.3 µM, 1 µM) of Compound 1 (in DMSO), 1 µM of control compound AZD9291 (a third-generation, oral, irreversible mutation-selective EGFR inhibitor) (in DMSO), 1 µM of control compound CO-1686 (a third-generation, oral, irreversible mutation-selective EGFR inhibitor) (in DMSO) for 24 hours. The cells were collected, washed twice with 1×PBS buffer, fixed with 75% ethanol at −20° C. for 24 hours, washed again with 1×PBS buffer twice. 0.5 mL 1×PBS buffer and 0.5 mL of PI dyeing liquor (purchased from BD Bioscience, USA) were added to the cells, and the cells were placed in the dark at 37° C. for dyeing 15 minutes and the cell cycle distribution was detected by flow cytometry (BD FACS Calibur). The results were shown in FIG. 3.

Experimental results were shown in FIG. 3: after 24 hour's treatment on human non-small cell lung cancer cells A549 (expressing wild-type EGFR gene), little effect of Compound 1 on cell cycle of the human non-small cell lung cancer cells A549 (expressing wild-type EGFR gene) was observed. In contrast, there was significant cell cycle arrest in G0-G1 in other four types of cells.

Example 65

Experimental Results of Compound 1 in Mouse Models of Human Non-Small Cell Lung Cancer Cells PC-9 and Human Non-Small Cell Lung Cancer Cells H1975

1). 27 4-6 week-old Bal b/c female mice were purchased from Shanghai SLAC Experimental Animal Co., Ltd., and were raised in a SPF-level laboratory. Drinking water and padding were both subjected to aseptic processing via high-pressure disinfection, and all operations of the mice were conducted under aseptic conditions;

2). $5\times10^6$ human non-small cell lung cancer cells PC-9 or human non-small cell lung cancer cells H1975 (purchased from ATCC) were respectively injected subcutaneously at left side back of all mice at Day 0;

3). Methyl cellulose (HKI) solvent (6 mice); Compound 1 at a dosage of 25 mg/kg mouse weight (7 mice); Compound 1 at a dosage of 50 mg/kg mouse weight (7 mice);

Compound 1 at a dosage of 100 mg/kg mouse weight (7 mice) were orally administrated to corresponding mice daily from Day 15;

4). Length/width of subcutaneous tumors were measured daily with a vernier caliper from Day 15 and mice weight was recorded daily to examine the effects of Compound 1 on mice weight;

5). Mice were sacrificed on Day 36 and subcutaneous tumors were taken out and weighed for comparison;

6). Tumor tissue specimens were prepared into protein lysate samples for further usage;

7). The growth trend of subcutaneous tumors from Day 16 to Day 36 was derived, and tumor volume was calculated as length×width×width/2 mm³.

Figure 4A:
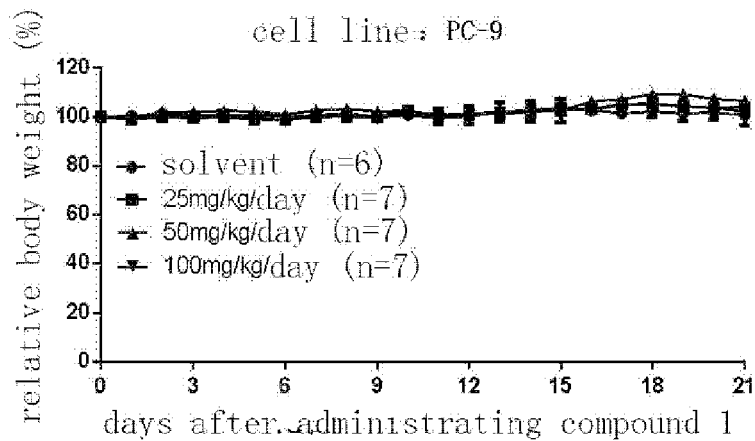
FIG. 4a shows the relative body weight that varies with time.
Figure 4B:
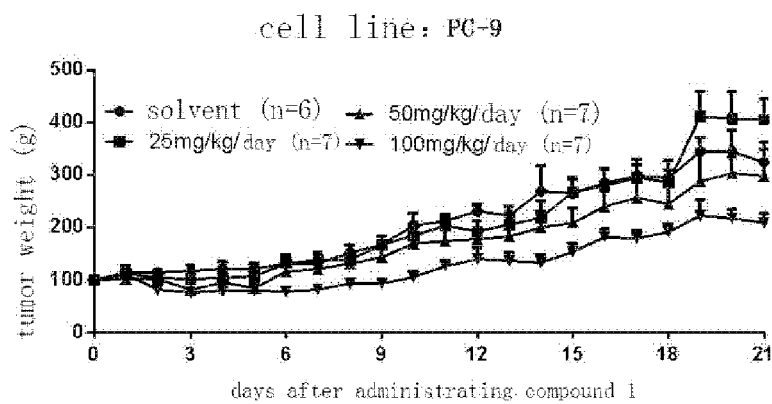
FIG. 4b shows the relative size of tumors that vary with time.
Figures 4C, 4D:
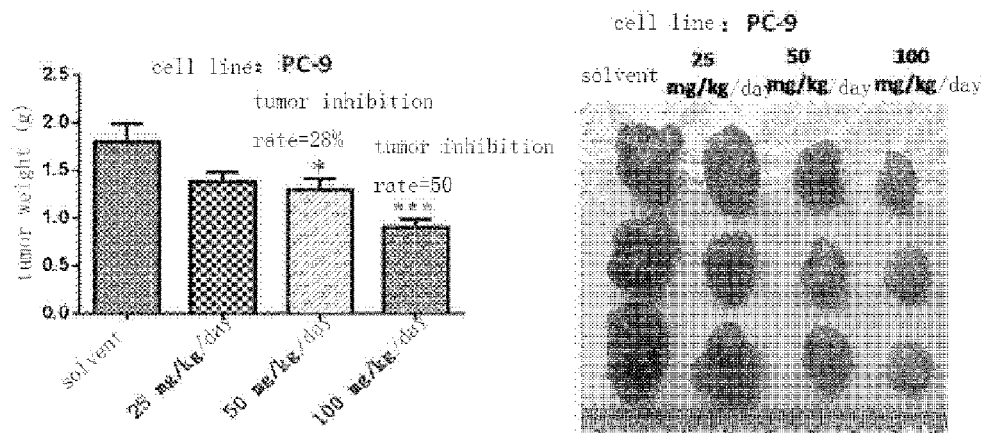
FIG. 4c shows the tumor weights after Day 21.
FIG. 4d shows the tumor photos captured from mice treated with difference concentrations of Compound 1 and the solvent control for 21 days.
Figure 5A:
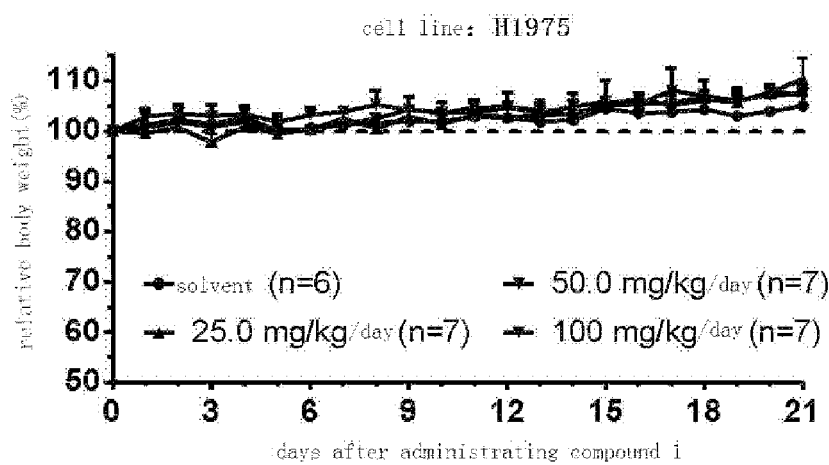
FIG. 5a shows the relative body weight that varies with time.
Figure 5B:
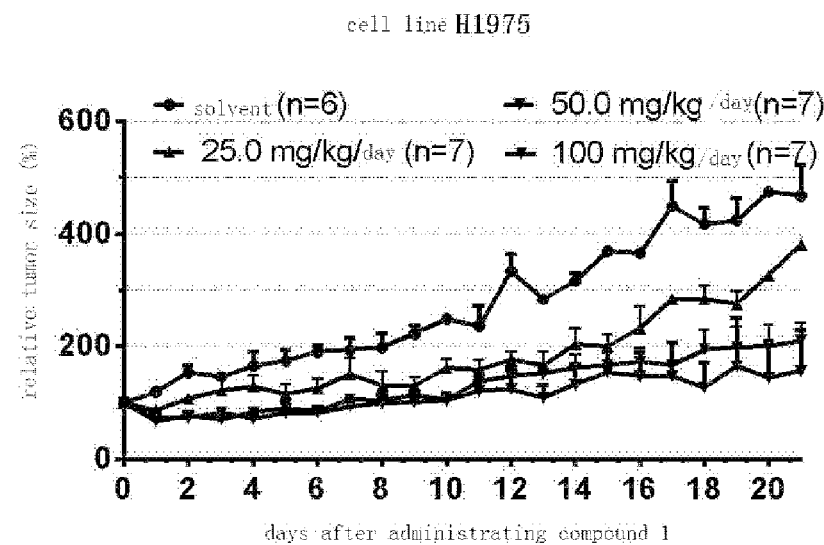
FIG. 5b shows the relative size of tumors that vary with time.
Figure 5C:
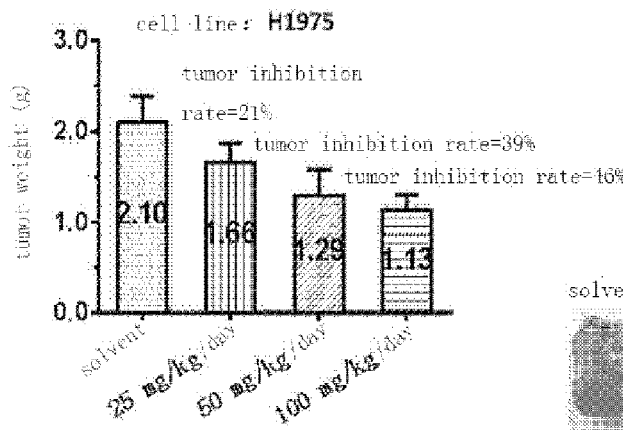
FIG. 5c shows the tumor weights after Day 21.
Figure 5D:
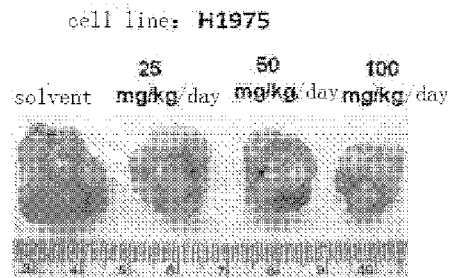
FIG. 5d shows the tumor photos captured from mice treated with difference concentrations of Compound 1 and the solvent control for 21 days.

The experiments revealed that, as shown in FIG. 4, in the mouse tumor model of human non-small cell lung cancer cells PC-9, a very significant effect in tumor suppression was obtained and reduce in mice was not observed after four days of compound administration when Compound 1 was administrated at a dosage of 25 mg/kg; when the dosage was 50 mg/kg, a very significant effect in tumor suppression was also obtained and reduce in mice were not observed after four days of compound administration, with a tumor inhibition rate of 28% at Day 21; when the dosage was 100 mg/kg, a very significant effect was obtained on Day 2 and tumor suppression was increased with no reduce in body weight, and the tumor inhibition rate reached as high as 50% at Day 21.

In addition, it was revealed in the experiments that, as shown in FIG. 5, in the mouse tumor model of human non-small cell lung cancer cells H1975, a very significant effect was obtained and reduce in mice was not observed when Compound 1 was administrated at a dosage of 25 mg/kg, with a tumor inhibition rate of 21% at Day 21; when the dosage of Compound 1 was 50 mg/kg, a very significant effect in tumor suppression was also obtained and reduce in mice were not observed after four days of compound administration, with a tumor inhibition rate of as high as 39% at Day 21; when the dosage was 100 mg/kg, a very significant effect was obtained, giving obvious tumor suppression, and reduce in mice were not observed after four days of compound administration, with a tumor inhibition rate of as high as 46% at Day 21.

INDUSTRIAL APPLICABILITY

The present invention provides a kinase inhibitor against wild-type and mutant EGFR which may be used for treating non-small cell lung cancer, especially for treating drug-resistant non-small cell lung cancer with EGFR T790M mutation and/or EGFR L858R mutation and/or EGFR delE746_A750 mutation. Therefore, it may be prepared as corresponding medicaments and has industrial applicability.

While the invention has been described in detail herein, the invention is not limited thereto and modifications may be made by those skilled in the art based on the principles of the invention, and thus, all modifications in accordance with the principles of the invention are to be understood as within the protection scope of the invention.

The invention claimed is:

1. A compound having a structure of Formula (II), or a pharmaceutically acceptable salt or solvate thereof:

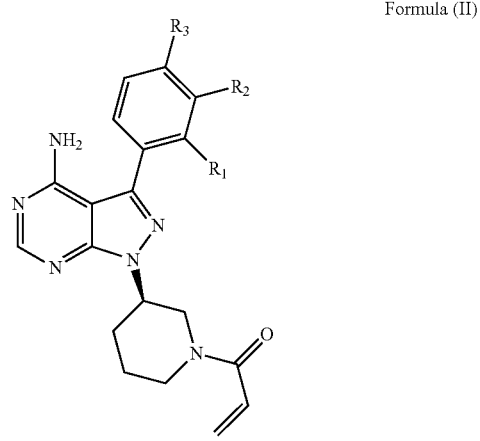

Formula (II)

wherein, $R_1$ is hydrogen;

$R_2$ is selected from the group consisting of halogen and $C_{1-8}$ alkyl;

$R_3$ is selected from the group consisting of halogen, benzyloxy, and heteroarylalkoxy, and $R_3$ is optionally substituted with 1 to 3 $R_6$;

each $R_6$ is independently selected from the group consisting of hydrogen, halogen, $C_{1-8}$ alkyl, $C_{1-8}$ haloalkyl, $C_{1-8}$ alkoxy, cyano, and methanesulfonyl;

wherein the compounds within Formula (II) are in an (R) configuration in the absence of corresponding compounds having an (S) configuration.

2. The compound or a pharmaceutically acceptable salt or solvate of claim 1, wherein $R_3$ is substituted with 1 to 3 $R_6$, and each $R_6$ is independently selected from the group consisting of hydrogen, halogen, $C_{1-8}$ alkyl, and $C_{1-8}$ alkoxy.

3. The compound or a pharmaceutically acceptable salt or solvate of claim 1, wherein $R_2$ is selected from the group consisting of fluoro, chloro, and methyl.

4. The compound or a pharmaceutically acceptable salt or solvate of claim 3, wherein $R_2$ is chloro.

5. The compound or a pharmaceutically acceptable salt or solvate of claim 1, wherein $R_3$ is selected from the group consisting of: fluoro, chloro; benzyloxy, m-fluorobenzyloxy, o-fluorobenzyloxy, p-fluorobenzyloxy, 3,4-difluorobenzyloxy, 2,5-difluorobenzyloxy; pyridin-2-ylmethoxy, 6-methylpyridin-2-ylmethoxy, 4-methoxy-3,5-dimethylpyridin-2-ylmethoxy, 6-methylpyridin-3-ylmethoxy, thiazol-2-ylmethoxy, imidazol-2-ylmethoxy, and (1-methyl-1H-imidazol-2-yl)methoxy.

6. The compound or a pharmaceutically acceptable salt or solvate of claim 5, wherein $R_3$ is selected from the group consisting of m-fluorobenzyloxy, pyridin-2-ylmethoxy, and 6-methylpyridin-2-ylmethoxy.

7. The compound or a pharmaceutically acceptable salt or solvate of claim 1, which is selected from the groun consisting of Compound 1

Compound 2

Compound 9

Compound 12

Compound 13

Compound 14

Compound 15

Compound 17

Compound 18

Compound 21

Compound 22

Compound 23

Compound 28
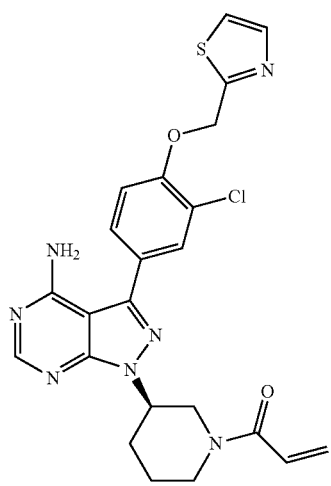
Compound 29
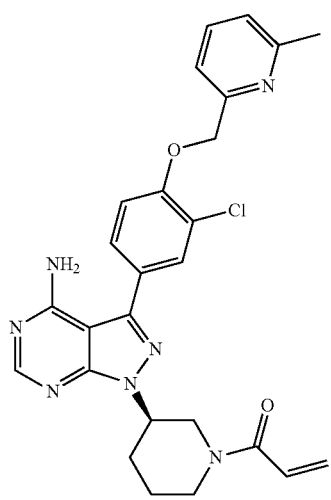
Compound 30
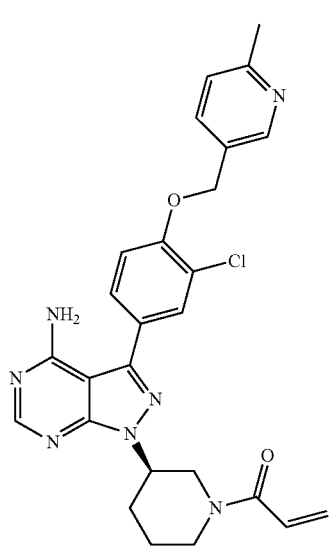
Compound 31
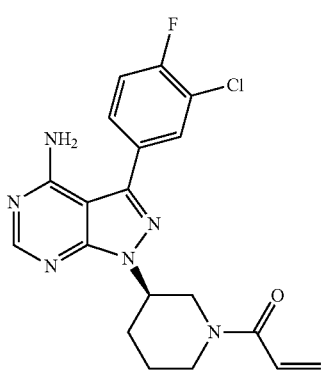
Compound 33
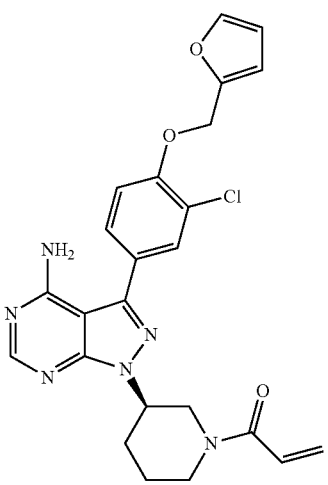
Compound 36
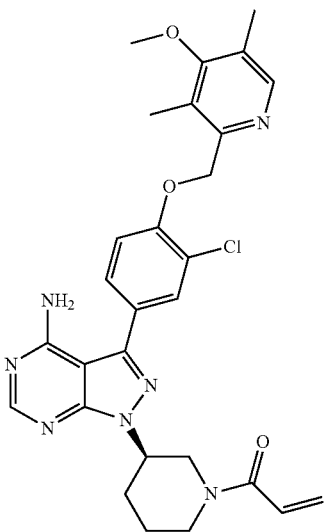

Compound 37
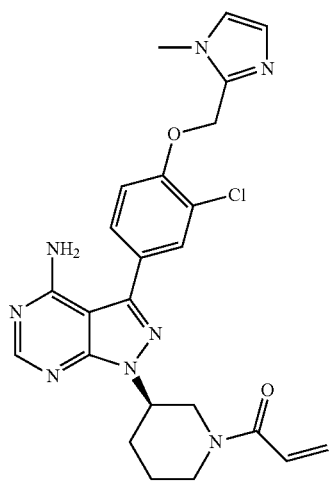
Compound 39
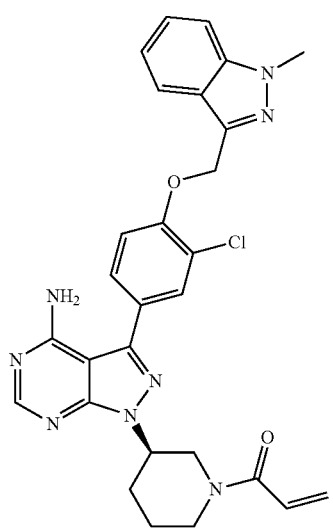
Compound 41
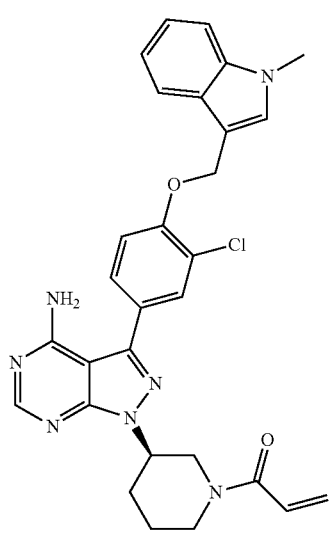
Compound 42
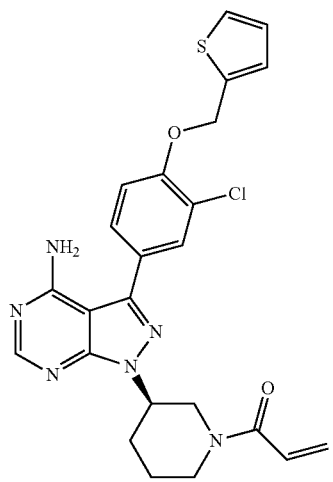
Compound 43
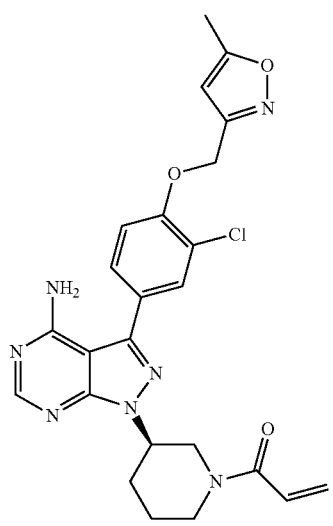
Compound 44
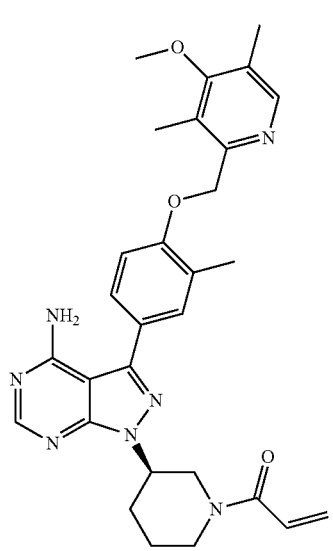

Compound 45
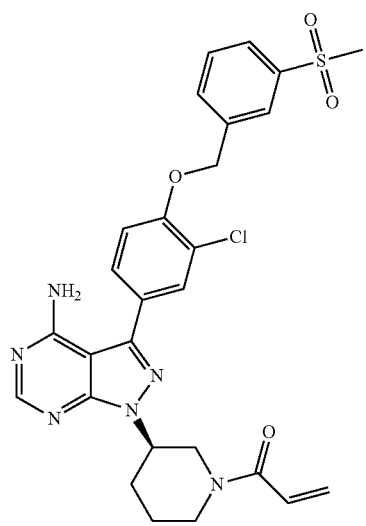
Compound 47
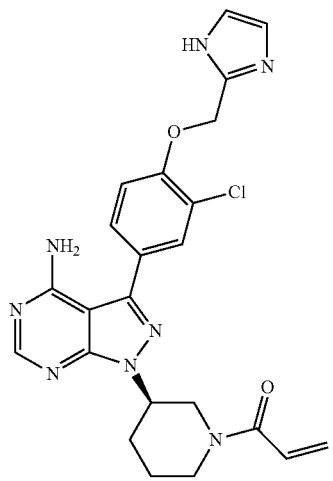
Compound 56
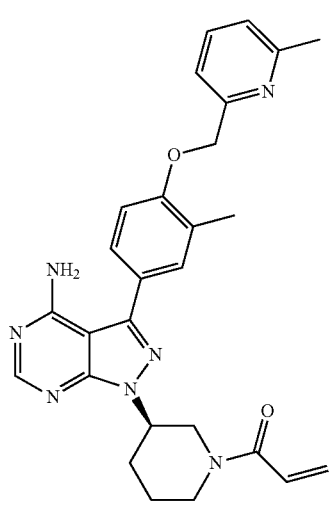
Compound 57
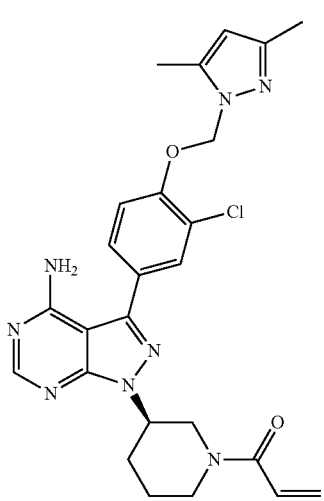
Compound 58
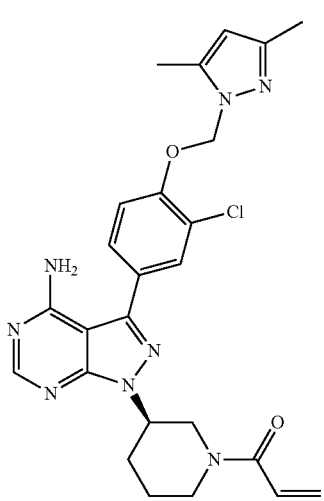
Compound 59
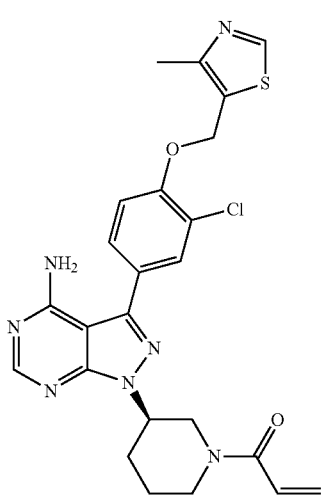

-continued

Compound 60

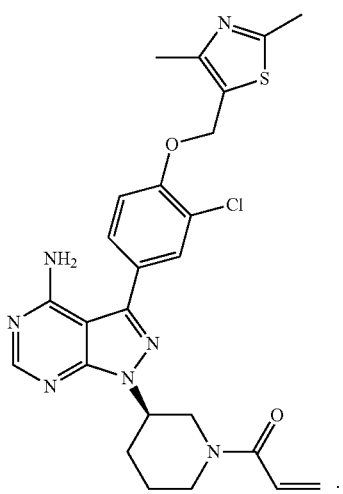

8. A method for treating or improving a disease, disorder, or condition modulated by or otherwise affected by tyrosine kinase activity or in which tyrosine kinase activity is implicated in a subject, comprising administering the compound or a pharmaceutically acceptable salt or solvate thereof according to claim 1 to the subject, wherein the disease, disorder, or condition is at least one proliferative disease selected from the group consisting of non-small cell lung cancer, small cell lung cancer, lung adenocarcinoma, lung squamous carcinoma, skin cancer, and combinations thereof.

9. The method according to claim 8, wherein the non-small cell lung cancer refers to drug-resistant human non-small cell lung cancer with wild-type EGFR and/or EGFR T790M mutation and/or EGFR L858R mutation and/or EGFR delE746_A750 mutation.

10. A method for inhibiting EGFR tyrosine kinase activity in a subject, comprising administering the compound or a pharmaceutically acceptable salt or solvate thereof according to claim 1 to the subject.

11. A pharmaceutical composition comprising the compound or a pharmaceutically acceptable salt or solvate thereof according to claim 1, a pharmaceutically acceptable carrier or excipient, and one or more other therapeutic agents.

* * * * *